US010849987B2

(12) United States Patent
Yun et al.

(10) Patent No.: US 10,849,987 B2
(45) Date of Patent: Dec. 1, 2020

(54) COMPLEX OF ADENOVIRUS AND PAMAM-PEG-ERBITUX, AND USE THEREOF

(71) Applicant: INDUSTRY-UNIVERSITY COOPERATION FOUNDATION HANYANG UNIVERSITY, Seoul (KR)

(72) Inventors: Chae Ok Yun, Seoul (KR); A-Rum Yoon, Gyeonggi-do (KR)

(73) Assignee: INDUSTRY-UNIVERSITY COOPERATION FOUNDATION HANYANG UNIVERSITY

( * ) Notice: Subject to any disclaimer, the term of this patent is extended or adjusted under 35 U.S.C. 154(b) by 98 days.

(21) Appl. No.: 16/125,070

(22) Filed: Sep. 7, 2018

(65) Prior Publication Data

US 2019/0134218 A1    May 9, 2019

Related U.S. Application Data

(63) Continuation-in-part of application No. PCT/KR2017/002449, filed on Mar. 7, 2017.

(30) Foreign Application Priority Data

Mar. 7, 2016 (KR) .................. 10-2016-0027309

(51) Int. Cl.
*A61K 47/69* (2017.01)
*A61K 48/00* (2006.01)
*A61K 47/50* (2017.01)
*A61K 39/395* (2006.01)
*A61K 47/32* (2006.01)
*A61K 47/60* (2017.01)
*A61K 47/68* (2017.01)
(Continued)

(52) U.S. Cl.
CPC ........ *A61K 47/6901* (2017.08); *A61K 39/395* (2013.01); *A61K 47/32* (2013.01); *A61K 47/50* (2017.08); *A61K 47/595* (2017.08); *A61K 47/60* (2017.08); *A61K 47/6849* (2017.08); *A61K 48/00* (2013.01); *A61P 35/00* (2018.01)

(58) Field of Classification Search
None
See application file for complete search history.

(56) References Cited

FOREIGN PATENT DOCUMENTS

| CN | 201410373077.3 | 7/2014 |
| KR | 10-2009-0013343 | 2/2009 |
| KR | 10-2003-0090918 | 12/2013 |

OTHER PUBLICATIONS

Yoon et al., Journal of Controlled Release 231 (2016) 2-16 (Year: 2016).*

(Continued)

*Primary Examiner* — Karl J Puttlitz
(74) *Attorney, Agent, or Firm* — Adsero IP

(57) ABSTRACT

The present invention relates to a complex of an antitumor adenovirus coated with ErbB-PEG-PAMAM and the use thereof. When using the complex of the present invention, a tumor cell-specific gene transfer effect by an excellent tumor cell infiltration ability is excellent, hepatotoxicity is low, a blood flow retention time is prolonged. Thus, the complex of the present invention can be used as a pharmaceutical composition for the treatment of a tumor and a gene therapy agent which can be administered systemically.

14 Claims, 21 Drawing Sheets

(51) Int. Cl.
    A61K 47/59    (2017.01)
    A61P 35/00    (2006.01)

(56) References Cited

OTHER PUBLICATIONS

Capasso et al., "The Evolution of Adenoviral Vectors through Genetic and Chemical Surface Modifications", Viruses, 2014, vol. 6, pp. 832-855.

Grunwald et al., "EGFR-Targeted Adenovirus Dendrimer Coating for Improved Systemic Delivery of the Theranostic NIS Gene", Molecular Therapy-Nucleic Acids, 2013, vol. 2, 10 pages.

Saxena, "Synthesis and Characterization of Doxorubicin Carrying Cetuximab-Pamam Dendrimer Bioconjugates", Thesis from the Graduate School at VCU Scholars Compass, downloaded from http://scholarscompass.vcu.edu/etd/2788, 2012.

Vetter, Dissertation, Buhl, Deutschland, 2013, "Non-covalent dendrimer- and polymer-based modifications of adenovirus capsids for enhanced transduction of cancer cells", 124 pages.

Vetter et al., "Adenoviral Vectors Coated with PAMAM Dendrimer Conjugates Allow CAR Independent Virus Uptake and Targeting to the EGF Receptor", Molecular Pharmaceutic 2013, vol. 10, 606-618.

Yoon et al., "Antitumor effect and safety profile of systemically delivered oncolytic adenovirus complexed with EGFR-targeted PAMAM-based dendrimer in orthotopic lung tumor model", Journal of Controlled Release, vol. 231, (2016), pp. 2-16.

Choi et al., "Polymeric oncolytic adenovirus for cancer gene therapy", J. Control Release (2015), http://dx.doi.org/10.1016/j.jconrel.2015.10.009.

Korean Office Action for application 10-2017-0028903, dated Feb. 25, 2019, 9 pages (in Korean language).

* cited by examiner

1. PBS
2. oAd/DCN-shMet
3. oAd/DCN-shMet/PP
4. oAd/DCN-shMet/PPE (A)

1. PBS
2. oAd/DCN-shMet
3. oAd/DCN-shMet/PP
4. oAd/DCN-shMet/PPE

COMPLEX OF ADENOVIRUS AND PAMAM-PEG-ERBITUX, AND USE THEREOF

This application claims priority to and is a Continuation-In-Part of PCT/KR2017/002449 (WO2017/155281), filed on Mar. 7, 2017 entitled "COMPLEX OF ADENOVIRUS AND PAMAM-PEG-ERBITUX, AND USE THEREOF", which application claims priority to and the benefit of Korean Patent Application No. 10-2016-0027309 filed on Mar. 7, 2016, the disclosures of which are incorporated herein by reference in their entirety. Any disclaimer that may have occurred during the prosecution of the above-referenced applications is hereby expressly rescinded, and reconsideration of all relevant art is respectfully requested.

BACKGROUND

1. Field of the Invention

The present invention relates to a complex of an adenovirus and PAMAM-PEG-Erbitux and a use of the complex. More particularly, the present invention relates to a tumor-specific gene transfer using a complex of an adenovirus and PAMAM-PEG-Erbitux, and an antitumor composition or gene therapeutic agent comprising the complex.

2. Discussion of Related Art

Lung cancer is one of the most commonly diagnosed and malignant types of cancer. It was estimated that 408,808 people in the United States were living with lung and bronchial cancer in 2014 [1]. According to 2014 cancer statistics from the NIH, the prognosis of lung cancer with conventional therapies, such as chemical and radiological treatments, is ineffective in eradication of lung cancers and a five-year survival rate is estimated at 15% [2]. Therefore, there is a substantial need for further research into the mechanism of lung cancer and development of novel and targeted therapeutics.

In order to overcome non-specificity of conventional chemotherapeutics, the molecular mechanism behind lung carcinogenesis was extensively studied and subsequently, lung cancer-targeted therapeutics were developed [3-5]. Activation of a receptor tyrosine kinase (RTK), such as epidermal growth factor receptor (EGFR) and tyrosine kinase receptor for hepatocyte growth factor (c-Met), induces cellular proliferation, differentiation, migration, and angiogenesis, ultimately contributing to lung cancer oncogenesis [6-9]. Due to high prevalence of aberrant EGFR expression in lung cancer, EGFR inhibitors have been extensively developed [10, 11]. Erbitux (ErbB), which is one of the EGFR inhibitors, is a well-documented and efficacious anti-EGFR monoclonal antibody (Ab) that has a high specificity toward EGFR [12-14]. ErbB induces potent growth inhibition of EGFR-expressing lung cancer cells and antitumor effects in preclinical lung cancer models, and now it is widely used to treat lung cancer patients [17, 18].

An oncolytic adenovirus (Ad) is widely regarded as a novel and promising alternative to traditional cancer therapy as it exhibits tumor selective replication, high rate of viral production, and a potent cytopathic effect [19, 20]. Further, "armed" oncolytic Ads expressing a therapeutic transgene have been extensively investigated to maximize the potency of an oncolytic Ad. Advantages of this approach are subsequent infection of neighboring cancer cells following lysis of cells and cancer-selective amplification of a therapeutic gene by a conditionally replicative Ad [21]. Among many candidates of therapeutic transgenes for oncolytic Ads, genes targeting RTK could be a promising candidate for targeted lung cancer therapy. To this end, the inventors have previously reported an oncolytic Ad expressing c-Met-specific short-hairpin RNA (shMet) to induce cancer specific downregulation of c-Met signaling, resulting in therapeutic induction of autophagy and tumor growth inhibition.

Despite the many advantages of an armed oncolytic Ad, as a monotherapeutic agent, its efficacy results in poor clinical outcomes. Systemic administration of a naked Ad can induce severe hepatotoxicity due to its native tropism which contributes to nonspecific liver sequestration [23-25]. Furthermore, the highly immunogenic viral capsid of a naked Ad triggers rapid induction of innate and adaptive immune responses against the Ad by the host, resulting in rapid blood clearance and a potentially fatal inflammatory response [28, 29]. These drawbacks of systemically administered Ad-mediated gene therapy can be overcome by chemical modification of the Ad surface with non-immunogenic nanomaterials such as polymers, liposomes, and peptides [30-32]. Synthetic cationic dendritic poly(amidoamine) (PAMAM) has been reported. Synthetic cationic dendritic poly(amidoamine) (PAMAM) efficiently binds with an anionic viral capsid to enhance cellular uptake of an Ad as well as reduce an Ad's immunogenicity [33, 34]. However, there are still problems in that the highly cationic PAMAM dendrimer has narrow clinical applications due to PAMAM's poor biocompatibility and biodegradability and causes nonspecific internalization into non-targeted cells and severe toxicity [35, 36].

Therefore, there is a desperate need for development of methods and materials capable of overcoming the limitation of clinical use of naked adenoviruses through low hepatotoxicity, an excellent therapeutic effect, and the like.

SUMMARY OF THE INVENTION

The present invention provides a complex of an adenovirus with ErbB-conjugated and PEGylated PAMAM (PPE) in order to overcome the limitation of clinical use of naked adenoviruses.

To this end, the present inventor confirmed that by using an oncolytic Ad forming a complex with ErbB-conjugated and PEGylated PAMAM (PPE), the toxicity of the PAMAM dendrimer is reduced and a specific and excellent antitumor effect against EGFR-expressing lung cancer is possessed, thereby completing the present invention.

In order to solve the problems, the present invention provides a virus-polymer complex in which a polymer, which is poly(amidoamine) (PAMAM) to which PEG and Erbitux (ErbB) are bound, binds to the surface of a virus.

Further, the present invention provides a pharmaceutical composition including: a therapeutically effective amount of the polymer-virus complex; a therapeutic gene; and a pharmaceutically acceptable carrier.

In addition, the present invention provides a composition for gene delivery, including the polymer-virus complex.

The virus-polymer complex of the present invention has an excellent tumor cell-specific gene transfer effect due to an excellent tumor cell infiltration ability, low hepatotoxicity, and a prolonged flow retention time, and thus can be used as a pharmaceutical composition for the treatment of a tumor and a gene therapy agent which can be administered systemically by overcoming drawbacks of an adenoviral vector in the related art.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

The present invention provides a virus-polymer complex in which a polymer, which is poly(amidoamine) (PAMAM) to which PEG and Erbitux (ErbB) are bound, binds to the surface of a virus.

Further, the present invention provides a pharmaceutical composition including: a therapeutically effective amount of the polymer-virus complex; a therapeutic gene; and a pharmaceutically acceptable carrier.

In addition, the present invention provides a composition for gene delivery, including the polymer-virus complex.

Hereinafter, the present invention will be described in more detail.

According to an aspect of the present invention, the present invention provides a virus-polymer complex in which a polymer, which is poly(amidoamine) (PAMAM) to which polyethylene glycol (PEG) and Erbitux (ErbB) are bound, binds to the surface of a virus.

The poly(amidoamine) (PAMAM) is one of the dendrimers having branched amine and amide groups, and is a cationic polymer exhibiting a spherical shape. The PAMAM polymer may have a problem of cytotoxicity, and the like when clinically used, and the problem may be solved by binding to the PEG.

Figure 1A:
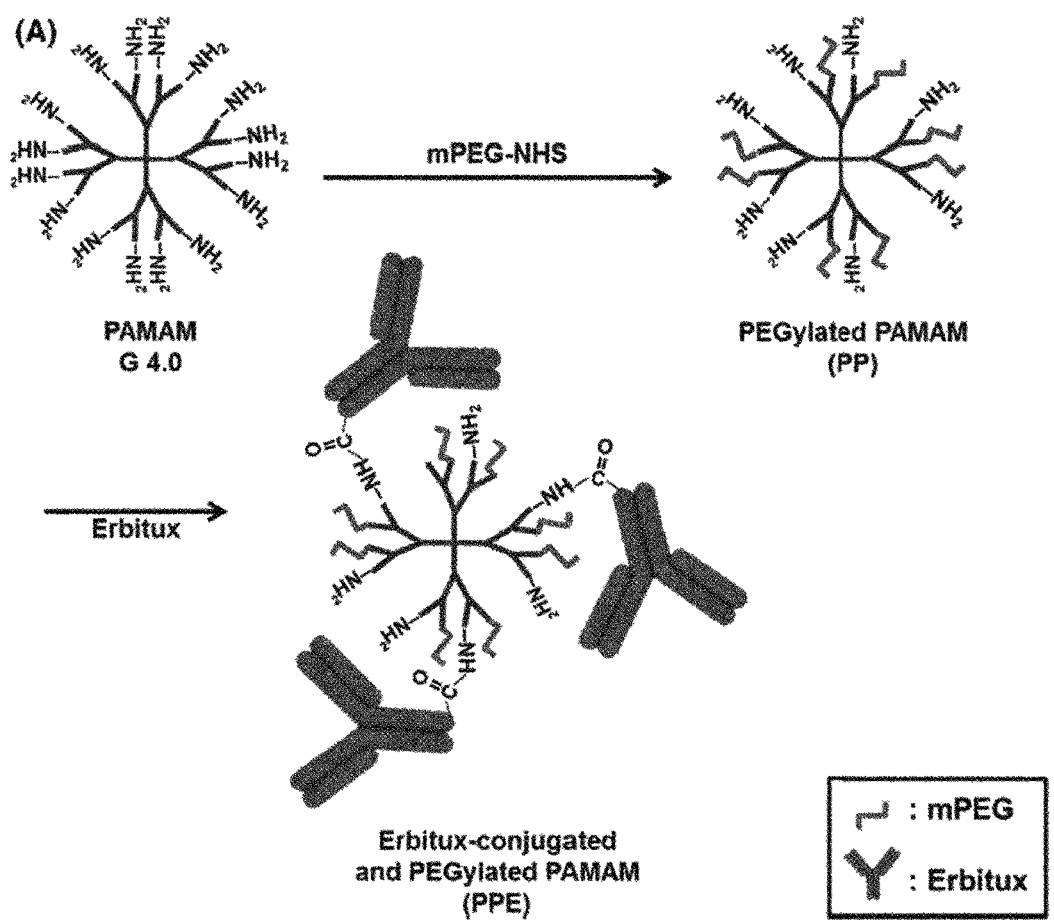
FIG. 1A is a schematic view showing an Erbitux (ErbB)-conjugated and PEGylated PAMAM dendrimer.
Figure 1B:
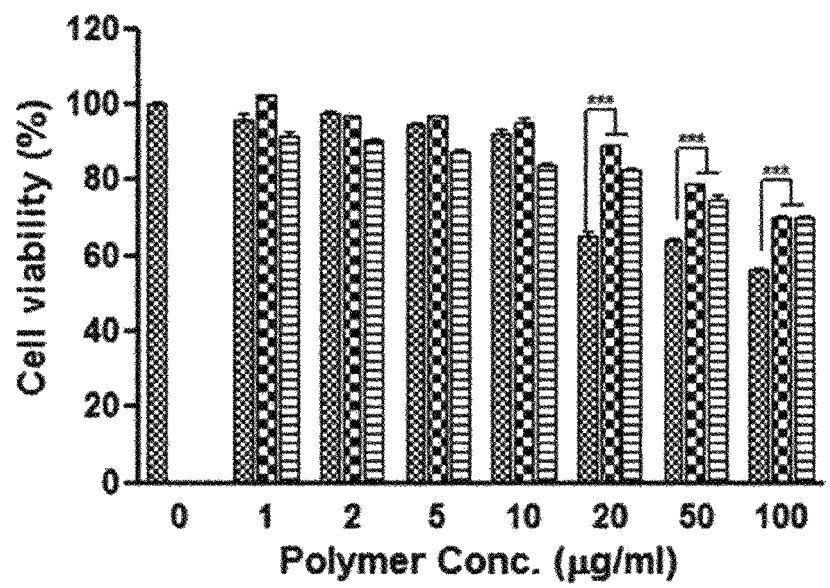
FIG. 1B shows results identifying cytotoxicity caused by a polymer according to an Example of the present invention. The data shows values obtained by subjecting each cell line (A549 or MCF7) to three independent experiments in triplicate, and bars represent mean±SD (***P<0.001).
Figure 1B:
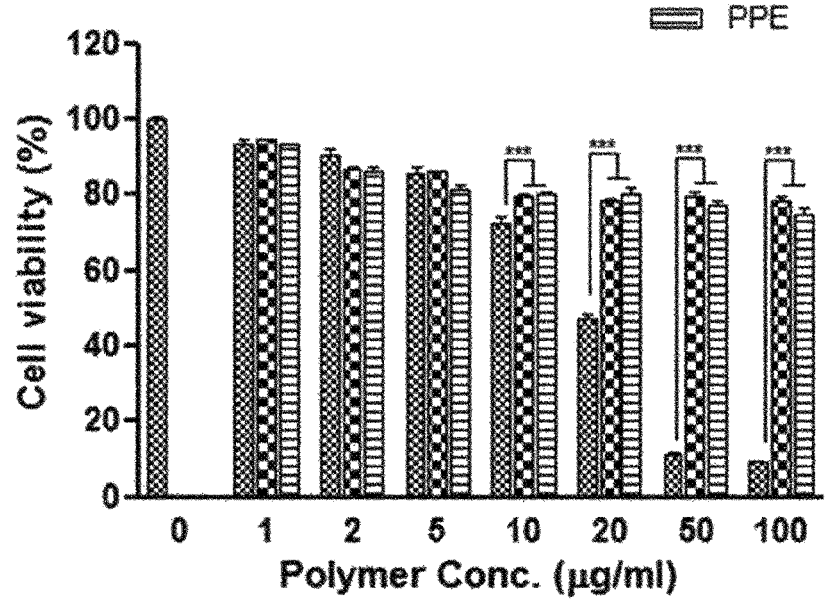

The polyethylene glycol (PEG) is a polymer used to cause cell fusion, and in an Example of the present invention, it was confirmed that when the PAMAM of the present invention binds to the PEG, the surface charge of a cationic polymer is reduced, and as a result, toxicity is reduced (FIG. 1B). In this respect, the PAMAM of the present invention may be PAMAM to which PEG is bound, that is, PEGylated PAMAM.

The binding of PAMAM and PEG may be performed by a typical PEGylation method in the art of the present invention, and specifically, the PAMAM and the PEG may be bound to each other by reacting polyethylene-NHS with free amine groups of a PAMAM dendrimer.

Figure 4A:
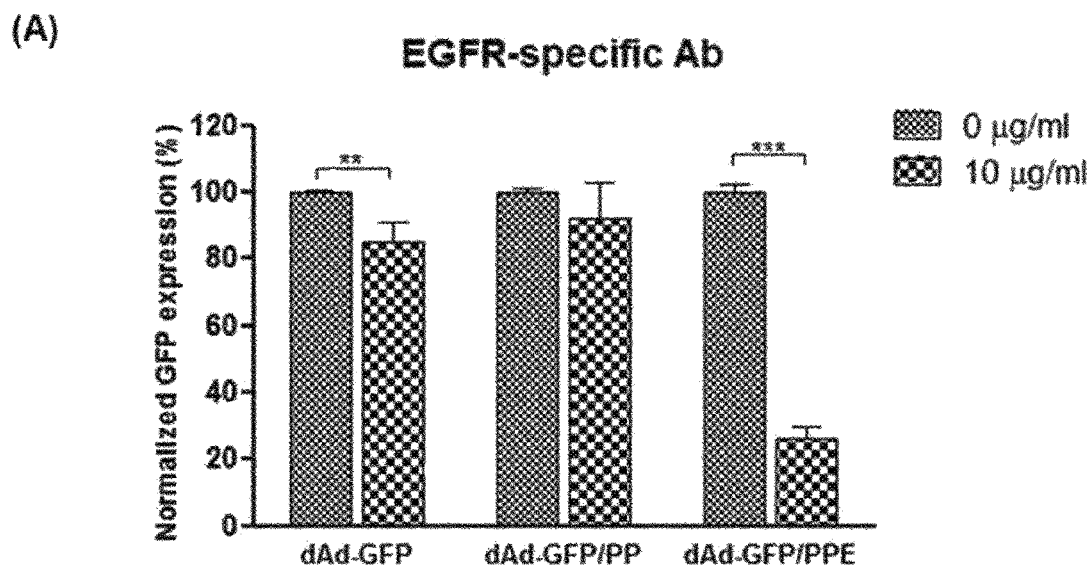
FIG. 4A shows a competition assay with an EGFR-specific antibody, confirming EGFR-mediated cell entry of complexes according to an Example of the present invention, the data shows values obtained by performing three independent experiments in triplicate, and bars represent mean±SD (**P<0.01).
Figure 4B:
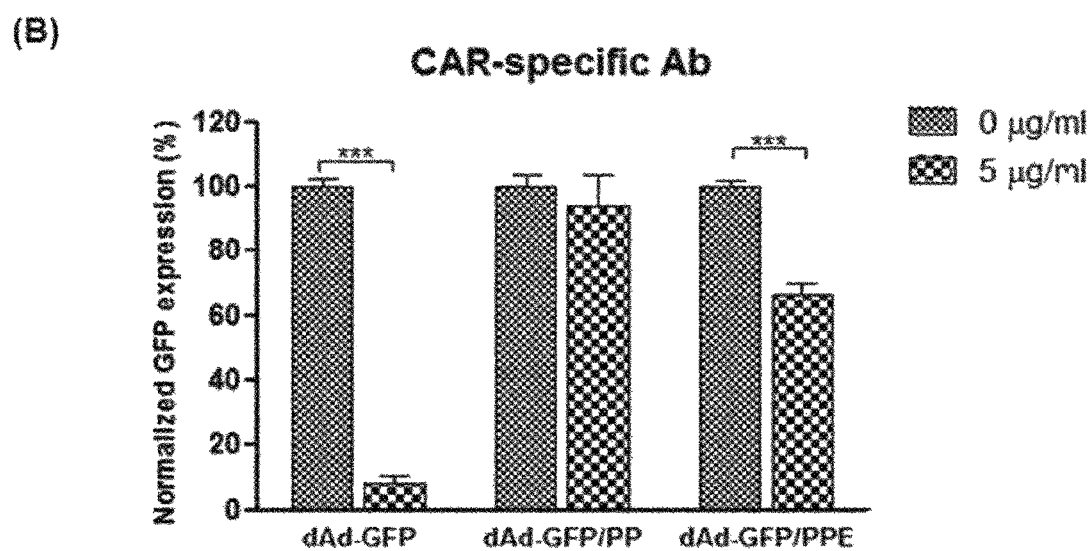
FIG. 4B is a competition assay with CAR-specific Ab, identifying EGFR-mediated cell entry of complexes (dAd-GFP, dAd-GFP/PP, and dAd-GFP/PPE) according to an Example of the present invention, the data shows values obtained by performing three independent experiments in triplicate, and bars represent mean±SD (**P<0.001).

Erbitux (ErbB) is an antibody specific to an EGF receptor (EGFR), and is one of the tumor cell targeting therapeutic agents known to be effective for colorectal cancer, head and neck cancer, and the like. As the PAMAM binds to the surface of a virus, the virus-polymer complex of the present invention may have a cancer cell targeting ability by also including an antibody targeting the EGFR simultaneously while solving the problems of immunogenicity and the like due to the viral capsid. In particular, since the complex of the present invention has Erbitux on the surface thereof, it was confirmed that it was possible to enhance a targeting ability and a cell infiltration ability with respect to EGFR-positive cells, and the enhanced abilities were better than infiltration effects by a CAR receptor which is an original receptor of an adenovirus (FIGS. 4A and 4B).

The binding of the PAMAM and the ErbB may be performed by a typical method, and is not limited to the method. As an example, ErB and PAMAM may be conjugated to each other. As in an Example of the present invention, the PAMAM and the ErB may be bound to each other by reacting the ErB with an amine group on the surface of the PAMAM.

The polymer of the present invention may be preferably a polymer in which ErB is conjugated to PEGylated PAMAM. More specifically, the polymer of the present invention may be in the form of a polymer complex in which PEG binds to some branched amine groups of PAMAM and ErbB binds to the other amine groups.

The polymer of the present invention is in a form where the polymer binds to the surface of a virus, and may form a virus-polymer complex. Specifically, the bond of the polymer and the virus may be an electrostatic bond between a positively charged polymer and a negatively charged surface of the virus. For the virus-polymer complex according to one aspect of the present invention, the surface of the virus is coated with a polymer to reduce endogenous immunogenicity associated with naked virus administered by conventional route. Additionally, the polymer increases the blood residence time of the virus while attenuating hepatic uptake and hepatotoxicity of the virus. Accordingly, the virus-polymer complex of the present invention may be effective for systemic administration. Further, the polymer-virus complex of the present invention improves a cell infiltration ability by electrostatic interaction between a negatively charged cell membrane and a positively charged polymer encapsulating the surface of virus.

Accordingly, the virus-polymer complex of the present invention may be a complex for systemic administration.

The complex may have a virus:polymer molar ratio of 1:more than $1 \times 10^4$ to less than $1 \times 10^6$. The transduction ability of the virus is significantly excellent, so that a complex satisfying the molar ratio of the virus and the polymer may be effectively used for both gene delivery and gene therapy, which use the complex of the present invention. The molar ratio may be more specifically $1:3 \times 10^4$ to $5 \times 10^5$, $1:4 \times 10^4$ to $4 \times 10^5$, or $1:4 \times 10^4$ to $3 \times 10^5$. The number of moles of the virus may be obtained by dividing the number of viruses (VP) by Avogadro's number of $6.023 \times 10^{23}$. As an example, since the number of moles of viruses of $1 \times 10^8$ (VP) becomes $1.66 \times 10^{-16}$ moles when divided by Avogadro's number ($6.023 \times 10^{23}$), the case where the virus present at $1.66 \times 10^{-16}$ moles is calculated as 1 mol may be applied to the present invention. Accordingly, viruses of $1 \times 10^8$ (VP) may be included in 1 mole of virus at the molar ratio.

Figure 2A:
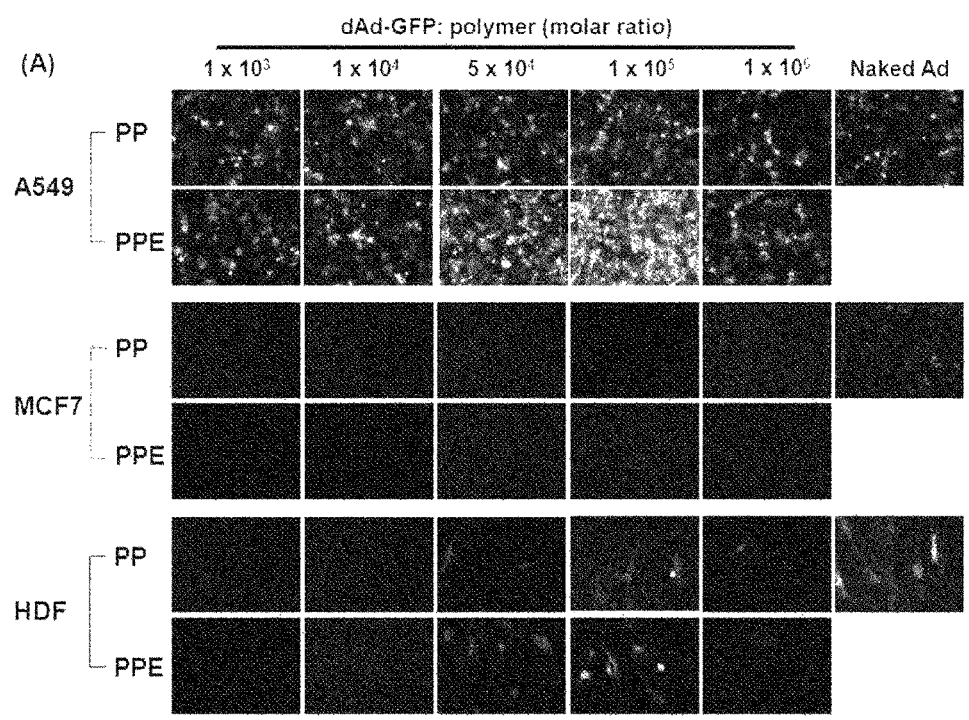
FIGS. 2A and 2B are results identifying EGFR-specific transduction efficiency of dAd-GFP/PPE according to an Example of the present invention, the data shows values obtained by performing three independent experiments in triplicate as results of analyzing GFP transduction efficiency of EGFR-positive (A549) cells or-negative (MCF7 or HDF) cells treated with dAd-GFP/PP or dAd-GFP/PPE, and naked dAd-GFP at various Ad:polymer ratios ($1\times10^3$, $1\times10^4$, $5\times10^4$, $1\times10^5$, and $1\times10^6$) by (A) a fluorescence microscope and (B) flow cytometry at 48 h post-transduction, and bars represent mean±SD.
Figure 2B:
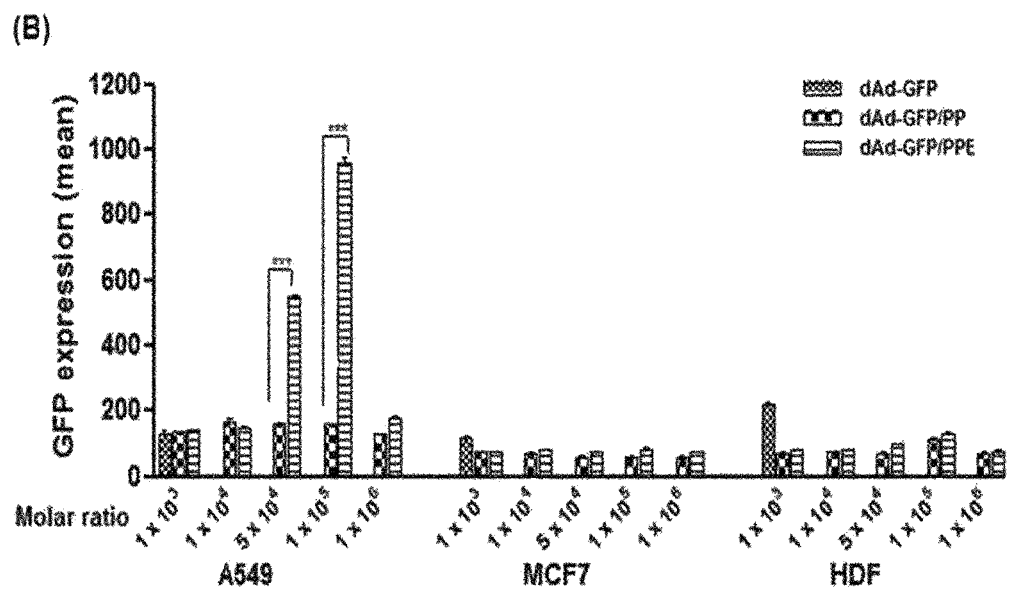
Figure 13:
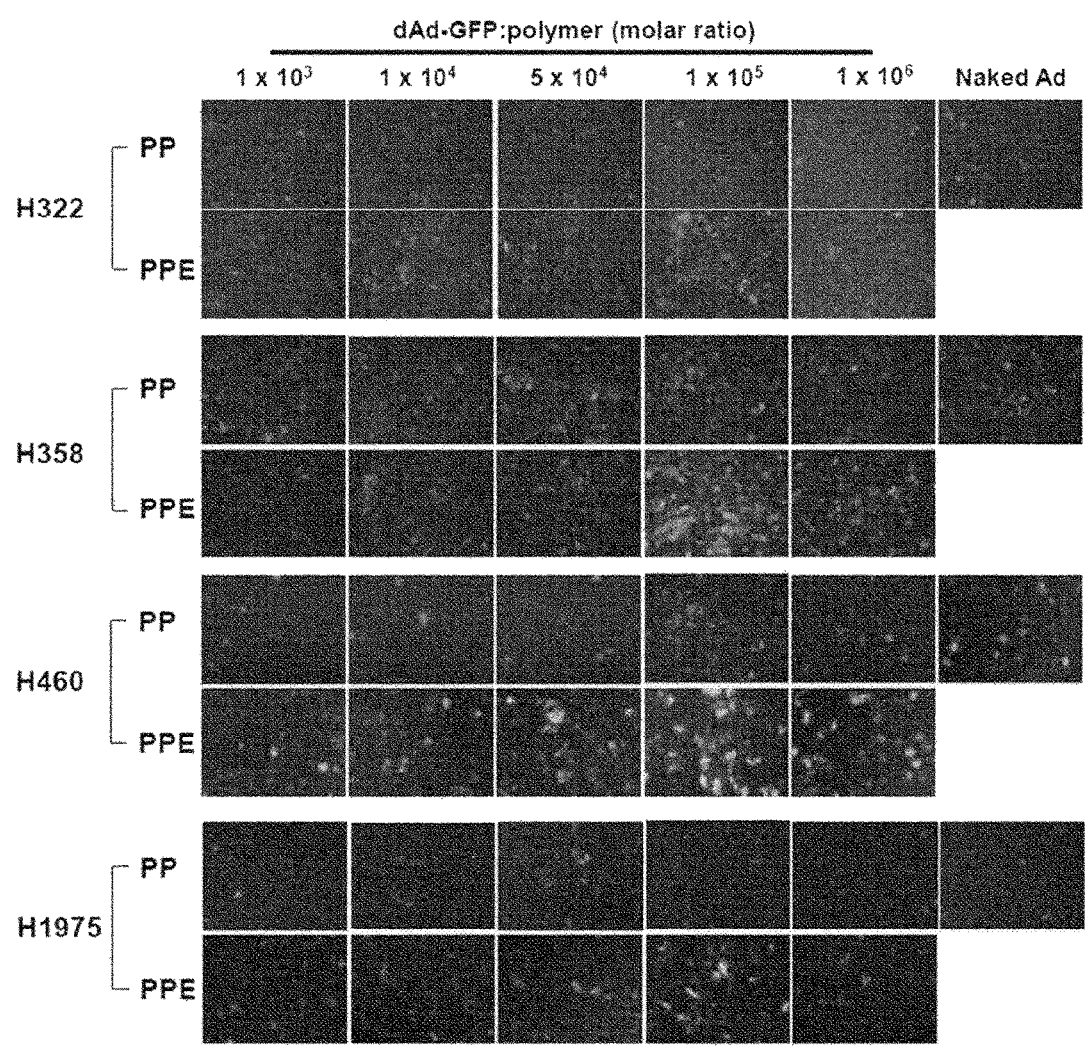
FIG. 13 is a graph comparing EGFR-specific gene delivery efficiencies for EGFR-positive lung cancer cells (H322, H358, H460, and H1975) of complexes having various molar ratios according to an Example of the present invention.

According to an Example of the present invention, it was confirmed that when the molar ratio of the virus and polymer of the complex satisfied the above range, the gene delivery efficiency was significantly excellent (FIGS. 2A, 2B, and 13).

The virus used in the polymer-virus complex of the present invention includes any virus, and specifically includes viruses as long as the viruses may be used for the treatment of diseases, such as therapeutic agents, vaccines, drug carriers, vectors, or gene delivery carriers. Preferably, the virus may be an anticancer virus. The anticancer virus is meant to include all viruses that are replication-competent, that is, infectious viruses, either wild-type or attenuated viruses as they are, or viruses used for cancer treatment by inserting any genes while maintaining infectivity. For example, the anticancer virus may be applied to an adenovirus, adeno associated virus (AAV) (Lashford L S., et al., Gene Therapy Technologies, Applications and Regulations Ed. A. Meager (1999)), a retrovirus (Gunzburg W H, et al., Gene Therapy Technologies, Applications and Regulations Ed. A. Meager, (1999)), a lentivirus (Wang G. et al., J. Clin. Invest. 104(11):R55-62 (1999)), herpes simplex virus (Chamber R., et al., Proc. Natl. Acad. Sci USA 92:1411-1415 (1995)), vaccinia virus (Puhlmann M. et al., Human Gene Therapy 10:649-657 (1999)), a reovirus, a poxvirus (GCE, NJL, Krupa M, Esteban M., The poxvirus vectors MVA and NYVAC as gene delivery systems for vaccination against infectious diseases and cancer Curr Gene Ther 8(2):97-120 (2008)), the Semliki forest virus, a polymer (Hwang et al., In vitro and In vivo Transfection Efficiency of Human Osteoprotegerin Gene using Non-Viral Polymer Carriers., Korean J. Bone Metab. 13(2):119-128 (2006)), liposome (Methods in Molecular Biology, Vol 199, S. C. Basu and M. Basu (Eds.), Human Press 2002), a nanomaterial or niosome, but is not limited thereto.

According to exemplary embodiments of the present invention, it was experimentally confirmed that in the case of a complex in which a ErbB-PEG-PAMAM is bound to the surface of an adenovirus, the transduction efficiency was excellent, and the therapeutic effects were excellent.

i. Adenovirus

An adenovirus has been frequently used as a gene transfer vector due to its moderate genome size, ease of manipulation, high titer, wide range of target cells and excellent infectivity. Both ends of the genome contain an inverted terminal repeat (ITR) of 100-200 bp, which is a cis-element essential for DNA replication and packaging. The E1 regions (E1A and E1B) of the genome encode proteins that regulate transcription and transcription of a host cell gene. The E2 regions (E2A and E2B) encode proteins involved in viral DNA replication.

Among the currently developed adenoviral vectors, a replication-incompetent adenovirus lacking the E1 region has been frequently used. Meanwhile, the E3 regions are removed from a typical adenoviral vector to provide a site into which an exogenous gene is inserted (Thimmappaya, B. et al., Cell, 31: 543-551 (1982); and Riordan, J R et al., Science, 245: 1066-1073 (1989)). Meanwhile, a target nucleotide sequence to be delivered into the cell is specifically inserted into a deleted E1 region (an E1A region and/or an E1B region, preferably an E1B region) or an E3 region, and more specifically, is inserted into a deleted E1 region.

The term "deletion" used in conjunction with a genomic sequence in the present specification has a meaning including complete deletion and partial deletion of the corresponding sequence.

Further, since the adenovirus may pack up to about 105% of a wild-type genome, about 2 kb can be additionally packaged (Ghosh-Choudhury et al., EMBO J., 6: 1733-1739 (1987)). Accordingly, the above-described exogenous sequences inserted into an adenovirus may be additionally bound to the genome of the adenovirus.

Adenoviruses have 42 different serotypes and subgroups of A-F. Among them, adenovirus type 5 belonging to the subgroup C is the most suitable starting material for obtaining the adenoviral vector of the present invention. Biochemical and genetic information on adenovirus type 5 is well known.

An exogenous gene delivered by the adenovirus is replicated in the same manner as an episome, and the genetic toxicity with respect to the host cell is very low.

ii. Retrovirus

A retrovirus has been frequently used as a gene delivery vector because the retrovirus may insert its genes into the genome of a host and may deliver a large amount of exogenous genetic materials, and the spectrum of cells which can be infected is broad.

In order to construct a retroviral vector, a target nucleotide sequence to be delivered is inserted into the genome of a retrovirus instead of the sequence of the retrovirus to produce a replication-incompetent virus. In order to produce a virion, a packaging cell line that includes the gag, pol, and env genes but does not have the long terminal repeat (LTR) and Ψ sequences is constructed (Mann et al., Cell, 33: 153-159 (1983)). When a recombinant plasmid including a target nucleotide sequence to be delivered and LTR and Ψ sequences are introduced into the cell line, the Ψ sequence enables the production of an RNA transcript of the recombinant plasmid, the transcript is packaged into a virus, and the virus is released into a medium (Nicolas and Rubinstein "Retroviral vectors," In: *Vectors: A survey of molecular cloning vectors and their uses*, Rodriguez and Denhardt (eds.), Stoneham: Butterworth, 494-513 (1988)). A medium containing the recombinant retrovirus is collected and concentrated, and thus is used as a gene delivery system.

Gene delivery using a second-generation retroviral vector has been published. According to Kasahara et al. *Science*, 266: 1373-1376 (1994), a mutant of the Moloney murine leukemia virus (MMLV) was prepared, and herein, a chimeric protein having new binding characteristics was produced by inserting an erythropoietin (EPO) sequence into an envelope site. The gene delivery system of the present invention may also be prepared according to the strategy of constructing the second-generation retroviral vector as described above.

iii. AAV Vector

Adeno-associated virus (AAV) may be used for the gene delivery system of the present invention because the adeno-associated virus (AAV) may infect non-dividing cells and has an ability to infect a variety of cell types. A detailed description on the preparation and use of an AAV vector is disclosed in detail in U.S. Pat. Nos. 5,139,941 and 4,797,368.

Typically, the AAV virus is prepared by simultaneously transforming a plasmid containing a target gene sequence located beside two AAV terminal repeats (McLaughlin et al., *J. Virol.*, 62: 1963-1973 (1988); and Samulski et al., *J. Virol.*, 63:3822-3828 (1989)) and an expression plasmid containing a wild-type AAV coding sequence having no terminal repeat (McCarty et al., *J. Virol.*, 65: 2936-2945 (1991)).

iv. Other Viral Vectors

Other viral vectors may also be used in the present invention. For example, vectors derived from the vaccinia virus (Puhlmann M. et al., *Human Gene Therapy* 10:649-657 (1999); Ridgeway, "Mammalian expression vectors," In: *Vectors: A survey of molecular cloning vectors and their uses*. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer*. New York: Plenum Press, 117-148 (1986) and Coupar et al., *Gene*, 68:1-10 (1988)), lentiviruses (Wang G. et al., *J. Clin. Invest.* 104(11):R55-62 (1999)), the herpes simplex virus (Chamber R., et al., *Proc. Natl. Acad. Sci USA* 92:1411-1415 (1995)), reoviruses (Nature 1960; 187:72-73, Br J Cancer. 2006; 95:1020-7, J Natl Cancer Inst. 2001; 93:903-12, Cancer Res. 2002; 62:1696-701), poxviruses (Oncogene 2010; 29:3990-3996), and the Semliki Forest virus may also be used in the present invention.

The complex of the present invention may include a therapeutic gene.

In the present invention, the therapeutic gene refers to a gene (polynucleotide sequence) capable of encoding a polypeptide capable of exhibiting therapeutic or prophylactic effects when expressed in cells. The therapeutic gene is not limited by a type of disease to be treated as long as the therapeutic gene may be included in the complex of the present invention, and may include a separate promoter for the expression of the gene. Examples thereof include a U6 promoter, an H1 promoter, a cytomegalo virus (CMV)

promoter, an adenovirus late promoter, a vaccinia virus 7.5K promoter, an SV40 promoter, a tk promoter of HSV, an RSV promoter, an EF1 alpha promoter, a metallothionein promoter, a beta-actin promoter, a promoter of a human IL-2 gene, a promoter of a human IFN gene, a promoter of a human IL-4 gene, a promoter of a human lymphotoxin gene, a promoter of a human GM-CSF gene, an inducible promoter, a cancer cell-specific promoter (for example, a TERT promoter, a PSA promoter, a PSMA promoter, a CEA promoter, an E2F promoter, and an AFP promoter), and a tissue-specific promoter (for example, an albumin promoter), but are not limited thereto. It is preferred that in an expression construct for expressing a transgene, a polyadenylation sequence binds downstream of the transgene. The polyadenylation sequence includes a bovine growth hormone terminator (Gimmi, E. R., et al., Nucleic Acids Res. 17:6983-6998 (1989)), an SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. Biol. 5:2104-2113 (1985)), or polyomavirus polyA (Batt, D. B and G. G. Carmichael, Mol. Cell. Biol. 15:4783-4790 (1995)), but is not limited thereto. Further, the therapeutic gene may be included either alone or in combination of two or more thereof.

The term "treatment" in the present invention refers to all actions which advantageously modify a disease or disorder, such as inhibition of the disease or disorder and reduction or alleviation of a symptom, through administration of the polymer-virus complex or composition according to the present invention, and encompasses "prevention" that suppresses the symptom or delays its occurrence.

A form in which the therapeutic gene is contained in the complex is not limited, and as an example, the form may be a virus that has been modified to have or/and have a therapeutic effect as it is, or may be included in a form of being bound to or delivered in the complex or virus of the present invention, but the form is not limited thereto. As a specific example, the therapeutic gene may be a cancer therapeutic gene exhibiting a therapeutic effect when expressed in cancer cells, and specifically, may include a drug-sensitizing gene, a tumor suppressor gene, an antigenic gene, a cytokine gene, a cytotoxic gene, a cytostatic gene, a pro-apoptotic gene, and an anti-angiogenic gene, but the therapeutic gene is not limited thereto.

The gene delivery carrier of the present invention may be used in a state where a target gene to be delivered is operatively linked to the above-described gene expression regulatory sequence. As used herein, the term "operatively linked" refers to a functional linkage between a gene expression regulatory sequence (for example: a promoter, a signal sequence, or an array of transcription regulation factor binding sites) and another nucleic acid sequence, and through the linkage, the regulatory sequence regulates the transcription and/or translation of the other nucleic acid sequence. The target gene, which is operatively linked to the gene expression regulatory sequence, is not particularly limited. For example, a gene to be expressed includes a gene derived from a genome of a gene delivery carrier, for example, an E1A gene, an E2 gene, an E3 gene, an E4 gene, or various therapeutic transgenes of adenoviruses. Examples of various therapeutic transgenes in the present invention include vastatin, p53, cytokines, immune-modulating genes, CD44v3/6, Adenovirus death protein (ADP), IFN-γ, HIF-1α siRNA, idolamine 2,3-dioxygenase2 (IDO2) siRNA, Wnt decoy protein, VEGF decoy protein, endostatin, VEGF Trap, VEGF siRNA, cMet siRNA, microRNA (microRNA-26a), miR-99a, miR-143, miR-193a-3p, miR-206, miR-506 (forkhead box Q1), IL-6, IL-12, shAkt1, shMYO6, carcinoembryonic antigen (CEA), sodium-iodine symporter (NIS), GM-CSF, cytosine deaminase (CD), HSV-TK, LMP2A/LMP1, IP-10/CXCL10, PF-4var/CXCL4L1, Super-cytosine deaminase, oncostatin M, a human-mouse chimeric antibody targeting CD 147, a humanized antibody, a zinc-finger protein targeting Lin28, a zinc-finger protein targeting VEGF, a zinc-finger protein targeting cMet, Cas 9 protein and guiding RNA, a TALEN protein, a TRAIL protein, or a phosphatase and tensin homolog protein (PTEN) encoding gene, and the therapeutic transgene of the present invention is not limited thereto. The above-described miR-99a targets mTOR, AKT1, and FGFR3, and miR-193a-3p targets a PSEN1 gene.

As used herein, the term "tumor suppressor gene" refers to a nucleotide sequence which is capable of suppressing a tumor phenotype or inducing apoptosis. The tumor suppressor gene useful in the practice of the present invention includes a p53 gene, an APC gene, a DPC-4/Smad4 gene, a BRCA-1 gene, a BRCA-2 gene, a WT-1 gene, a retinoblastoma gene (Lee et al., Nature, 1987, 329,642), an MMAC-1 gene, an adenomatous polyposis coli protein (U.S. Pat. No. 5,783,666), a deleted colon cancer (DCC) gene, an MMSC-2 gene, an NF-1 gene, a nasopharyngeal tumor suppressor gene located on chromosome 3p21.3 (Cheng et al. Proc. Nat. Acad. Sci, 95:3042-3047 (1998)), an MTS1 gene, a CDK4 gene, an NF-1 gene, an NF-2 gene, and a VHL gene. As used herein, the term "antigenic gene" refers to a nucleotide sequence which is expressed in target cells to produce a cell surface antigenic protein that can be recognized by the immune system. Examples of this antigenic gene include carcinoembryonic antigen (CEA) and p53 (Levine, A., International Patent Publication No. WO94/02167). In order to be easily recognized by the immune system, the antigenic gene can be bound to the MHC type I antigen.

In the present invention, an exogenous gene which can be delivered into cells by an antitumor adenovirus is a cancer therapeutic gene which induces death of cancer cells and ultimately degenerates a tumor, and examples thereof include a tumor suppressor gene, an immune-related gene [for example: a cytokine gene, a chemokine gene, and a costimulatory factor: an accessory molecule necessary for activation of T cells, such as B7.1 and B7.2)], an antigenic gene, a suicide gene, a cytotoxic gene, a cytostatic gene, a pro-apoptotic gene, and an anti-angiogenic gene, and are not limited thereto.

The suicide gene is a nucleic acid sequence expressing a material which induces cells to be easily killed by external factors or inducing toxic conditions in cells. Those well-known as the suicide gene are a thymidine kinase (TK) gene (U.S. Pat. Nos. 5,631,236 and 5,601,818). Cells expressing TK gene products are sensitive to selective death by administration of ganciclovir. The tumor suppressor gene refers to a gene encoding a polypeptide suppressing the formation of a tumor. The tumor suppressor gene is a gene naturally occurring in mammals, and it is believed that the deletion or inactivation of the gene is an essential prerequisite for tumor generation. Examples of the tumor suppressor gene include APC, DPC4, NF-1, NF-2, MTS1, WT1, BRCA1, BRCA2, VHL, p53, Rb, MMAC-1, MMSC-2, a retinoblastoma gene (Lee et al., Nature, 329:642 (1987)), an adenomatous polyposis coli protein (U.S. Pat. No. 5,783,666), a nasopharyngeal tumor suppressor gene located on chromosome 3p21.3 (Cheng et al. Proc. Nat. Acad. Sci, 95:3042-3047 (1998)), a deleted colon cancer (DCC) gene, a member of the INKAseries of a tumor suppressor gene including MTS1, CDK4, VHL, p110Rb, p16, and p21, and therapeutically effective fragments thereof (for example, p56Rb, p94Rb, and the like). It is to be understood by a person with ordinary skill in the art that all of the other known antitumor genes in addition to the exemplified genes can be used in the present invention.

As used herein, the term "antigenic gene" refers to a nucleotide sequence which is expressed in target cells to produce a cell surface antigentic protein that can be recognized by the immune system. Examples of the antigenic gene include a carcinoembryonic antigen (CEA), a prostate specific antigen (PSA), α-feto protein (AFP), and p53 (WO 94/02167). In order to be easily recognized by the immune system, the antigenic gene can be bound to the MHC type I antigen.

As used herein, the term "cytotoxic gene" refers to a nucleotide sequence which is expressed in cells to exhibit toxic effects. Examples of the cytotoxic gene include nucleotide sequences encoding *Pseudomonas* exotoxin, Ricin toxin, Diphtheria toxin, and the like.

As used herein, the term "cytostatic gene" refers to a nucleotide sequence which is expressed in cells to stop a cell cycle during the cell cycle. Examples of the cytostatic gene include p21, a retinoblastoma gene, an E2F-Rb fusion protein gene, a gene encoding a cyclin dependent kinase inhibitor (for example, p16, p15, p18, and p19), a growth arrest specific homeobox (GAX) gene (WO 97/16459 and WO 96/30385), and the like, and are not limited thereto.

Further, many therapeutic genes which can be usefully used for treating various diseases can also be delivered by the adenovirus of the present invention as a means for helping antitumor effects. Examples thereof include genes encoding cytokines (for example, interferon-alpha, -beta, -delta, and -gamma), interleukins (for example, IL-1, IL-2, IL-4, IL-6, IL-7, IL-10, IL-12, IL-19, and IL-20), and colony stimulating factors (for example, GM-CSF and G-CSF), and a chemokine group (monocyte chemoattractant protein 1 (MCP-1), monocyte chemoattractant protein 2 (MCP-2), monocyte chemoattractant protein 3 (MCP-3), monocyte chemoattractant protein 4 (MCP-4), macrophage inflammatory protein 1α (MIP-1α), macrophage inflammatory protein 1β (MIP-1β), macrophage inflammatory 1γ (MIP-1γ), macrophage inflammatory protein 3α (MIP-3α), macrophage inflammatory protein 3β (MIP-3β), EBI1-ligand chemokine (ELC), macrophage inflammatory protein 4 (MIP-4), macrophage inflammatory protein 5 (MIP-5), LD78β, RANTES, SIS-epsilon (p500), thymus activation-regulated chemokine (TARC), an eotaxin, I-309, human protein HCC-1/NCC-2, human protein HCC-3, mouse protein C10, and the like). Further, examples thereof include a gene expressing a tissue plasminogen activator (tPA) or urokinase and an LAL generating gene that provides sustained thrombotic effects to prevent hypercholesterolemia. In addition, many polynucleotides for treating cystic fibrosis, adenosine deaminase deficiency and viruses such as AIDS, and malignant and inflammatory diseases and conditions are known.

As used herein, the term "pro-apoptotic gene" refers to a nucleotide sequence which is expressed to induce programmed apoptosis. Examples of the pro-apoptotic gene include p53, adenovirus E3-11.6K (derived from Ad2 and Ad5) or adenovirus E3-10.5K (derived from Ad), the adenovirus E4 gene, Fas ligand, TNF-α, TRAIL, p53 pathway genes, and genes encoding caspases.

As used herein, the term "anti-angiogenic gene" refers to a nucleotide sequence which is expressed to release anti-angiogenic factors out of the cells. Examples of the anti-angiogenic factors include angiostatin, a suppressing factor of vescular endothelial growth factor (VEGF) such as Tie2 (PNAS, 1998, 95, 8795-800), endostatin, and the like.

As used herein, the term "metastasis-suppressing gene" refers to a gene suppressing metastasis by the migration and infiltration of cancer cells, and examples thereof include BRMS1, CRSP3, DRG1, KAI1, KISS1, NM23, and various tissue inhibitors of metalloproteinase (TIMPs).

As used herein, the term "immune-related gene" refers to all the genes regulating the expression of immune-related factors, and examples thereof include genes encoding cytokines (for example, interferon-alpha, -beta, -delta, and -gamma), interleukins (for example, IL-1, IL-2, IL-4, IL-6, IL-7, IL-10, IL-12, IL-17, IL-18, IL-19, IL-20, and IL-23), and colony stimulating factors (for example, GM-CSF and G-CSF), and a chemokine group (monocyte chemoattractant protein 1 (MCP-1), monocyte chemoattractant protein 2 (MCP-2), monocyte chemoattractant protein 3 (MCP-3), monocyte chemoattractant protein 4 (MCP-4), macrophage inflammatory protein 1α (MIP-1α), macrophage inflammatory protein 1β (MIP-1β), macrophage inflammatory 1γ (MIP-1γ), macrophage inflammatory protein 3α (MIP-3α), macrophage inflammatory protein 3β (MIP-3β), chemokine (ELC), macrophage inflammatory protein 4 (MIP-4), macrophage inflammatory protein 5 (MIP-5), LD78β, RANTES, SIS-epsilon (p500), thymus activation-regulated chemokine (TARC), an eotaxin, I-309, human protein HCC-1/NCC-2, human protein HCC-3, mouse protein C10, and the like), a costimulatory factor: an accessory molecule necessary for activation of T cells, such as B7.1 and B7.2, and the like.

The nucleotide sequence for the above-described purpose is available from a DNA sequence data bank, such as GenBank or EMBL.

As used herein, the term "antibody gene" refers to a nucleotide sequence producing a specific antibody capable of inducing apoptosis of cancer cells by binding to antigens preferentially or exclusively expressed in cancer cells, unlike normal cells. Examples of the antibody gene include a nucleotide sequence encoding anti-DR4/DR5, anti-CTLA-4, anti-PD-1, anti-PD-L1, anti-Her2/neu, anti-VEGF, anti-VEGFR, anti-cMet, anti-Survivin, anti-EGFR, anti-Wnt, anti-Ly49, and the like.

In an Example of the present invention, the tumor cell therapeutic effect by an oncolytic virus was identified by inserting a decorin gene and an Met gene into a viral vector such that the decorin gene and the Met gene could be simultaneously expressed (FIGS. 8A, 8B, 8C, and 8D).

According to another aspect of the present invention, the present invention provides a pharmaceutical composition including: a therapeutically effective amount of a polymer-virus complex; a therapeutic gene; and a pharmaceutically acceptable carrier.

Since the pharmaceutical composition of the present invention uses the above-described polymer-virus complex and/or therapeutic gene as an active ingredient, the description of the common content will be omitted in order to avoid the excessive complexity of the present specification.

The pharmaceutical composition may be for systemic administration or intravenous administration. A virus including the therapeutic gene in the related art has a disadvantage in that it is difficult to perform systemic administration due to induction of hepatotoxicity, an immune response, and the like. However, the present invention has advantages in that the present invention can prevent both innate and adaptive immune responses by being injected in the form of a poly-coated complex on the surface of a virus, and has an excellent therapeutic effect even for systemic administration due to low induction of hepatotoxicity and prolonged retention time in the body.

A pharmaceutical composition including a therapeutically effective amount of the polymer-virus complex of the present invention may be applied regardless of the type of disease. Specifically, since the pharmaceutical composition including the complex of the present invention may be applied variously to diseases to be applied according to various pharmaceutically active ingredients, the pharmaceutical composition including the complex may be applied for various uses without being limited to the type of disease. The pharmaceutically active ingredient is not limited in type, but may be included in the composition together with the complex of the present invention, or may be included in the composition in the form of being included in the complex of the present invention, and may be a therapeutic gene as an example. Accordingly, a pharmaceutical composition including a therapeutically effective amount of the polymer-virus complex of the present invention is included in the present invention regardless of the type of disease.

As described above, the pharmaceutical composition of the present invention is not limited by the type of disease, but may be preferably useful for anticancer treatment. From this viewpoint, the pharmaceutical composition may be an anticancer pharmaceutical composition.

In an exemplary embodiment of the present invention, as a result of identifying a tumor cell killing ability by using a polymer/virus complex coated with the polymer of the present invention, it was experimentally confirmed that the polymer/virus complex exhibited a higher tumor cell killing ability than non-coated viruses, the therapeutic gene was expressed in cells, and the expression thereof was increased. In particular, when compared with complexes which are not coated with a polymer, the pharmaceutical composition of the present invention had low hepatotoxicity and prolonged blood retention time, and it was confirmed that the pharmaceutical composition of the present invention had an excellent antitumor effect due to the high ratio of the pharmaceutical composition being accumulated in tumor cells while the inflow ratio to the liver was low throughout the Examples of the present invention.

When a gene exhibiting cancer cell killing efficacy is inserted into the polymer-virus complex included in the composition of the present invention, killing efficacy is exhibited against various cancer cells, so that the pharmaceutical composition of the present invention may be used for the treatment of cancer of the skin, digestive organs, urological organs, reproductive organs, respiratory organs, circulatory organs, the brain or nervous system. The composition may be specifically used for the treatment of laryngeal cancer, lung cancer, non-small cell lung cancer, colon cancer, bone cancer, pancreatic cancer, skin cancer, head or neck cancer, ovarian cancer, uterine cancer, rectal cancer, gastric cancer, anal cancer, breast cancer, fallopian tube cancer, endometrial cancer, cervical cancer, vaginal cancer, vulva cancer, Hodgkin's disease, esophageal cancer, small intestine cancer, endocrine cancer, thyroid cancer, parathyroid cancer, adrenal gland cancer, soft tissue sarcoma, urethral cancer, penile cancer, prostate cancer, chronic or acute leukemia, lymphocytic lymphoma, bladder cancer, renal or hydroureter cancer, renal cell carcinoma, renal pelvic carcinoma, central nervous system (CNS) tumors, primary central nervous system lymphoma, spinal cord tumors, liver cancer, bronchial cancer, nasopharyngeal cancer, brain stem glioma, pseudomyxoma peritonei, hepatoblastoma, testicular cancer, glioblastoma, cheilocarcinoma, ovarian germ cell tumors, basal cell carcinoma, multiple myeloma, gallbladder cancer, choroidal melanoma, carcinoma of the ampulla of Vater, peritoneal cancer, tongue cancer, small cell cancer, pediatric lymphoma, neuroblastoma, duodenal cancer, ureteral cancer, astrocytoma, meningioma, renal pelvic cancer, pudendum cancer, thymus cancer, pituitary adenoma, or the like, but is not limited thereto.

The cancer may be preferably a carcinoma showing EGFR-positivity, and more preferably a carcinoma appearing as a result of overexpression of EGFR. As a preferred example, the cancer may be lung cancer.

As used herein, the term "therapeutically effective amount" refers to an amount sufficient to achieve the pharmacological effect.

A pharmaceutically acceptable carrier included in the composition of the present invention is that typically used in formulation, and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto. The pharmaceutical composition of the present invention may additionally include a lubricant, a wetting agent, a sweetening agent, a flavoring agent, an emulsifier, a suspending agent, a preservative, and the like, in addition to the aforementioned ingredients.

As still another aspect of the present invention, the present invention provides a composition for gene delivery, which includes a polymer-virus complex.

When the polymer-virus complex of the present invention is used as a gene delivery carrier, the residual time in the blood stream after injection in vivo is long, and it is possible to prevent a phenomenon in which the polymer-virus complex of the present invention flows immediately into the liver, so that the gene delivery carrier may be delivered to a target site well, and thus has an excellent delivery effect.

As yet another aspect of the present invention, the present invention provides a method for treating an individual, including the step of administering the polymer-virus complex or the pharmaceutical composition to an individual in need of treatment in a pharmaceutically effective amount.

The pharmaceutical composition of the present invention is preferably parenterally administered, and may be administered, for example, by using intravenous administration, intraperitoneal administration, intramuscular administration, subcutaneous administration or topical administration. The pharmaceutical composition of the present invention is administered intraperitoneally to treat ovarian cancer and administered through the hepatic portal vein to treat liver cancer by an injection method, and in the case of breast cancer, the pharmaceutical composition may be administered by direct injection into a tumor mass, and in the case of colon cancer, the pharmaceutical composition may be administered by direct injection into an enema.

The term "pharmaceutically effective amount" of the present invention refers to an amount sufficient to treat a disease at a reasonable benefit/risk ratio applicable to any medical treatment. A suitable administration amount of the pharmaceutical composition of the present invention may vary depending on factors, such as formulation method, administration method, age, body weight, sex or disease condition of a patient, diet, administration time, administration route, excretion rate and response sensitivity, and a doctor with ordinary skill may readily determine and prescribe an administration amount effective for a desired treatment.

The term "individual" of the present invention includes animals such as horses, sheep, pigs, goats, camels, antelopes, and dogs, or humans, which have a disease whose symptoms can be alleviated by administration of the therapeutic composition according to the present invention. As the pharmaceutical composition according to the present invention is administered to the individual, a disease may be effectively prevented and treated. The treatment method according to the present invention may be a method for treating an animal other than a human, but the present invention is not limited thereto. That is, when considering that a human has a disease whose symptoms can be alleviated by administering the composition according to the present invention, the composition of the present invention may also be suitably used to treat a human disease.

The pharmaceutical composition of the present invention may be prepared in the form of a unit-dose or in a multi-dose container by being formulated using a pharmaceutically acceptable carrier and/or excipient according to a method that can be readily implemented by a person with ordinary skill in the art to which the present invention pertains. In this case, a dosage form may also be in the form of a solution in an oil or aqueous medium, a suspension or in the form of an emulsion, an extract, a powder, a granule, a tablet or a capsule, and the pharmaceutical composition of the present invention may additionally include a dispersant or a stabilizer.

The pharmaceutical composition of the present invention may be used as a single therapy, but may also be used in combination with another typical chemotherapy or radiation therapy, and when such combination therapy is implemented, cancer may be more effectively treated. A chemical therapeutic agent that can be used together with the composition of the present invention includes cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, methotrexate, and the like. A radiation therapy that can be used together with the composition of the present invention includes X-ray radiation, γ-ray radiation, and the like.

Examples

Materials and Methods

1. Preparation of Cells and Chemical Samples

A human embryonic kidney cell line (HEK293), an EGFR-positive human lung cancer cell line (A549), an EGFR-negative breast cancer cell line (MCF7), and EGFR-negative normal cells (HDF) were purchased from the American Type Culture Collection (ATCC, Manassas, Va.). Cells were cultured in high glucose Dulbecco's Modified Eagle's Media (DMEM; Gibco BRL, Waltham, Mass.) containing 10% fetal bovine serum (FBS; Gibco BRL) in an incubator at 37° C. with 5% $CO_2$. Methoxyl PEG succinimidyl carbonate NHS was purchased from Nanocs (New York, N.Y.). A G4 PAMAM cystamine core dendrimer (10 wt % in MeOH), N-hydroxysuccinimide (NHS), and 1-ethyl-3-(3-dimethylaminopropyl) carbodiimide hydrochloride (EDC) were purchased from the Sigma Chemical Co. (St Louis, Mo.). Erbitux® (anti-EGFR antibody) was purchased from Merck (Kenilworth, N.J.).

2. Preparation and Construction of Adenoviruses

The EGFR-dependent transduction efficiency was determined using a green fluorescent protein (GFP)-expressing replication-incompetent Ad (dAd-GFP) [29]. For the preparation of an oncolytic Ad co-expressing decorin (DCN) and shMet, the HRE enhancer was first inserted into a pDE1sp1B/Rd19 Ad E1 shuttle vector [40] to increase viral replication under hypoxic conditions, resulting in a pDE1sp1B/HRE-Rd19 Ad E1 shuttle vector. To insert the DCN expression cassette, the DCN gene was isolated from pCA14/DCN [41] using BglII, and then ligated into the pDE1sp1B/HRE-Rd19 E1 shuttle vector, thus preparing pDE1sp1B/HRE-Rd19/DCN. For homologous recombination, an XmnI-treated pDE1sp1B/HRE-Rd19/DCN Ad E1 shuttle vector was co-transformed into *Escherichia coli* BJ5183 with linearized Ad dE1-k35 [42], thus preparing a HRE-Rd19-k35/DCN oncolytic Ad plasmid.

To express shMet in the E3 region of an Ad, a shMet-expressing E3 shuttle vector (pSP72dE3-U6-shMet4; [22]) was linearized and co-transformed with a DCN-expressing oncolytic Ad vector (HRE-Rd19-k35/DCN) in *E. coli* BJ5183, thus preparing an HRERd19-k35/DCN/shMet oncolytic Ad plasmid. The proper homologous recombinant Ad plasmid DNA was digested with PacI and transfected into the 293 cells to generate an HRE-Rd19-k35/DCN/shMet oncolytic Ad (oAd/DCN-shMet). Replication-deficient dAd-GFP and replication-competent oAd/DCN-shMet were proliferated in 293 and A549 cells, respectively, and purified by CsCl gradient centrifugation. The numbers of viral particles (VP) were calculated from optical density measurements at 260 nm ($OD_{260}$) where an absorbance of 1 ($OD_{260}=1$) was equivalent to $1.1 \times 10^{12}$ VP/mL [43]. Purified viruses were stored at −80° C. until use.

3. Synthesis of ErbB-Conjugated and PEGylated PAMAM Dendrimer

Figure 10:
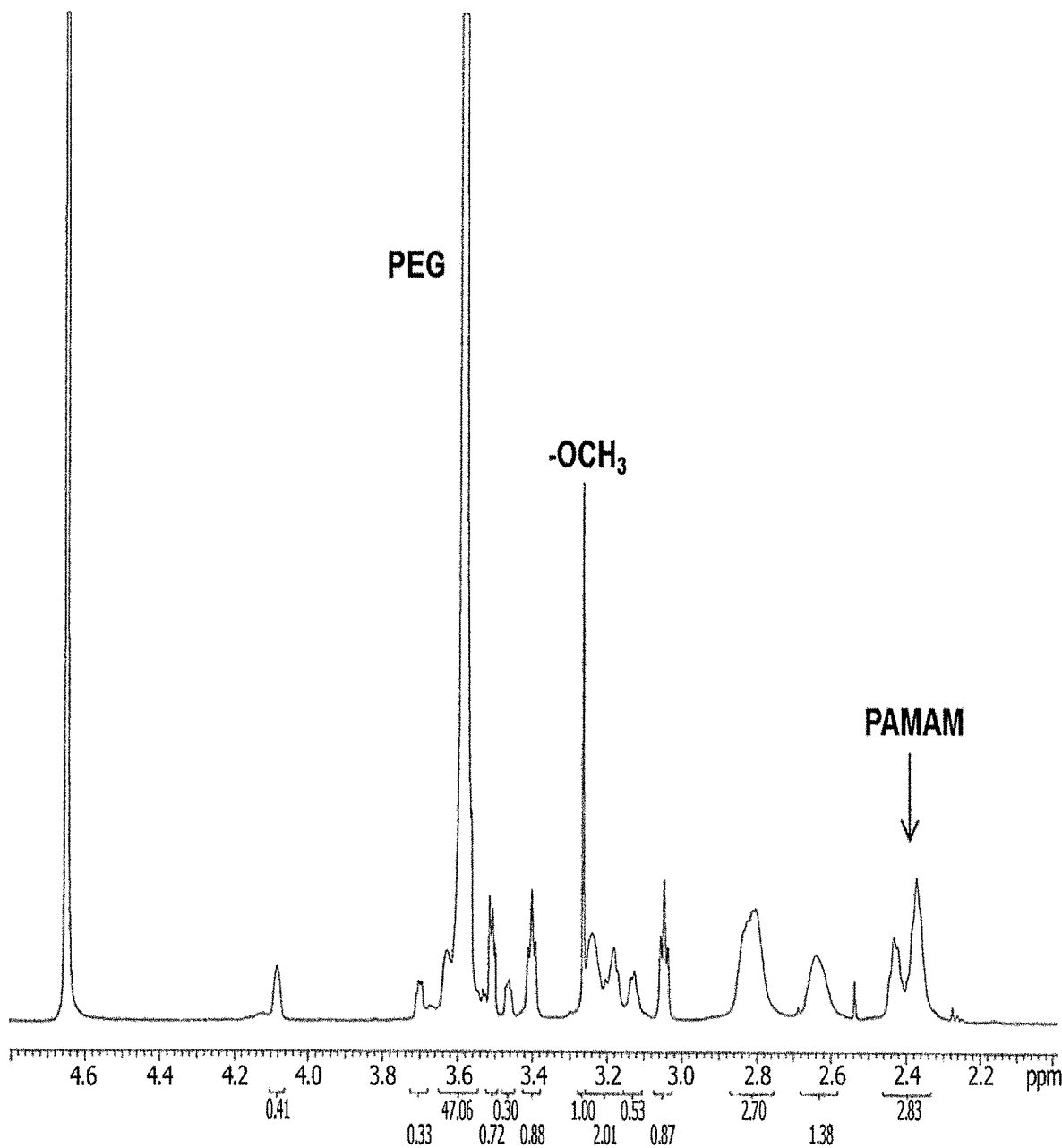
FIG. 10 shows a $^1$H NMR spectrum of PEGylated PAMAM according to an Example of the present invention.

For the preparation of PEGylated PAMAM (PP), conjugation of mPEG with G4 PAMAM was performed according to a previously disclosed procedure [44]. Briefly, a PAMAM dendrimer having free amine groups (0.56 μM) dissolved in PBS buffer was mixed with mPEG-NHS (18 μM), and resulting reaction mixture was stirred overnight at room temperature. The dendrimer product was purified by dialysis (MWCO 3.5 kDa) with double distilled water for 1 day and lyophilized to yield PEGylated PAMAM. A chemical structure of mPEG-PAMAM was analyzed by $^1$H NMR in $D_2O$ (Varian 600 MHz spectrometer; Varian Inc., Palo Alto, Calif., FIG. 10). The conjugation of PEG on PAMAM was confirmed by the presence of resonance peaks at 3.2 ppm and 3.4-3.6 ppm corresponding to the protons of a terminal —$OCH_3$ group of PEG and —$OCH_2$—$CH_2$ repeating units of PEG, respectively. The degree of PEGylation was estimated by using the proton integration method as described in a previous report [44]. The feed ratio of PAMAM:mPEG was 1:32. The observed ratio from $^1$H NMR was 1:24 (PAMAM:PEG), and the molecular weight of PEGylated PAMAM was calculated as 63.3 kDa.

For the preparation of ErbB-conjugated PP (PPE), 250 μL of EGFR-specific Ab (ErbB; 0.1 mg/mL) was mixed with 75 μL of EDC (5.0 mg/mL) and 50 μL of NHS (5.0 mg/mL) and dissolved in PBS, and then resulting solution was incubated at room temperature for 30 min to activate the carboxylic acid groups of the Ab. Then, 250 μL of the PP solution (6 mg/mL) was added to above solution and incubated at room temperature for 2 h. After the initial incubation period, the reaction mixture was further incubated at 4° C. overnight. Finally, unreacted reagents were removed by dialysis [45, 46].

4. Preparation and Characterization of Dendrimer-Coated (Complexed) Ad

For complexation of an Ad with either PP or PPE, both polymers were prepared in 1×PBS at a concentration of $1.7 \times 10^{-1}$ µM. A coated Ad at an Ad:polymer (PP or PPE) molar ratio of $1 \times 10^6$ was prepared by gently mixing $10^8$ VP of the Ad (100 µL) and a polymer (100 µL). For lower molar ratio samples, the $1.7 \times 10^{-1}$ µM polymer solutions were diluted by factor of 5, 10, 100, or 1,000 in 1×PBS, and 100 µL of the diluted polymers were reacted with $10^8$ VP of the Ad (100 µL), generating a polymer-coated Ad at a $5 \times 10^5$, $1 \times 10^5$, $1 \times 10^4$, or $1 \times 10^3$ molar ratio, respectively. The mixtures were allowed to electrostatically interact to form an Ad/dendrimer polyplex at room temperature for 30 min. For physiochemical characterization of each Ad formulation, the average particle size and surface charge of naked dAd-GFP, PP-complexed dAd-GFP (dAd-GFP/PP), or PPE-complexed dAd-GFP (dAd-GFP/PPE) were determined using the Zetasizer 3000HS (Malvern Instrument Inc., Worcestershire, UK) with a He—Ne laser beam (633 nm, fixed scattering angle of 90°) at room temperature [25, 29]. The average particle size and surface charge were computed as the average value of three independent measurements. Transmission electron microscopy (TEM) imaging of naked dAd-GFP, dAd-GFP/PP, or dAd-GFP/PPE complexes (molar ratio, $1 \times 10^1$) was carried out by incubating each sample on a TEM copper grid for 30 min at room temperature. Morphologies were subsequently characterized by TEM (JEM-2000EXll, JEPL, Nikon, Tokyo, Japan) at 150 kV.

5. Transduction Analysis for EGFR-Targeting Ability of dAd-GFP/PPE

To determine the EGFR-dependent transduction efficiency of dAd-GFP/PPE, cells (A549, H322, H358, H460, and H1975, MCF7, or HDF) were seeded at a density of $5 \times 10^4$ cells/well in a 24-well plate for 24 h prior to transduction. dAd-GFP was complexed with PP or PPE at various Ad:polymer molar ratios ($1 \times 10^3$ to $1 \times 10^6$). Following preparation of each treatment group, cells were treated with naked dAd-GFP, dAd-GFP/PP, or dAd-GFP/PPE. The specific treatment concentration for each cell was 20 MOI (A549), 5 MOI (H322), 0.1 MOI (H358), 1 MOI (H460), 1 MOI (H1975), 500 MOI (MCF7), or 100 MOI (HDF). And then, cells were incubated with serum-free DMEM for 4 h at 37° C.

Following incubation in serum-free DMEM, the cell culture medium was replaced with fresh DMEM containing 5% FBS and cells were further incubated for 48 h. GFP expression was observed by fluorescence microscopy (Olympus Optical) and quantitatively analyzed by flow cytometry (BD Biosciences, San Jose, Calif.).

6. Confirmation of Cellular Uptake and Co-Localization of dAd-GFP/PPE

Human cancer cells (A549 or MCF7) were seeded at a density of $2 \times 10^4$ cells/well on a sterile round coverslip placed in a 12-well plate prior to transduction with the Ad. Cells were treated with 100 MOI of fluorescein isothiocyanate (FITC)-labeled dAd-GFP or dendrimer (PP or PPE)-complexed FITC-labeled dAd-GFP for 2 h at 37° C. Subsequently, the cells were washed twice with PBS and fixed in 4% paraformaldehyde for 30 min. Nuclei and lysosomes were stained with DAPI and Lyso Tracker Red DND-99 (Thermo Fisher Scientific, Waltham, Mass.), respectively. After staining, coverslips were mounted on a slide. Samples were analyzed with a confocal laser scanning microscope (LSM510META, Carl Zeiss, Jena, Germany) according to a conventional method [22]. These images were semi-quantitatively analyzed by ImageJ software (version 1.50b; U.S. National Institutes of Health, Bethesda, Md.).

7. Competition Assay Using EGFR- or CAR-Specific Ab

In order to analyze the internalization mechanism of a naked Ad and dendrimer-complexed Ads, the inventors performed a competition assay with EGFR- or CAR-specific Ab on A549 (CAR- and EGFR-positive) cells. Cells were seeded into 24-well plates at a density of $1 \times 10^5$ cells/well and then incubated for 24 h at 37° C. On the following day, cells were pre-treated with or without ErbB Ab (10 µg/mL) or CAR-specific Ab (RmcB; 5 µg/mL) prepared in serum-free DMEM and then incubated for 1 h at 4° C. Following incubation, cells were treated with naked dAd-GFP, dAd-GFP/PP, or dAd-GFP/PPE. After treatment of each viral entity at an MOI of 100, cells were incubated for 48 h at 37° C. GFP expression was quantitatively assessed by flow cytometry (BD Biosciences).

8. Characterization of DCN and c-Met Expression

A549 cells were seeded into a 100-mm plate ($1 \times 10^6$ cells/plate; incubated in 5% fetal bovine serum-supplemented DMEM) and infected with oAd/DCN-shMet, oAd/DCN-shMet/PP, or oAd/DCN-shMet/PPE (0.5 MOI). Further, the cells were infected with PP or PPE as a control. At 36 h after infection, supernatants and cell pellets were obtained. The expression levels of DCN were determined from a collected supernatant by ELISA according to the manufacturer's instructions (DCN ELISA kit: Abcam, Ltd., Cambridge, UK). To measure c-Met expression levels, Western blot analysis was performed according to a conventionally known method [22]. In brief, cell pellets were lysed in an ice-cold radioimmunoprecipitation assay buffer (Elipis Biotech, Taejeon, Korea) containing a proteinase inhibitor cocktail (Sigma-Aldrich). Cell lysates were then centrifuged for 10 min and the total protein content of each sample was determined using a bicinchoninic acid (BCA) protein assay reagent kit (Pierce, Rockford, Ill.). 30 µg of proteins from the cell extracts were separated by 10% sodium dodecyl sulfate (SDS) polyacrylamide gel electrophoresis and then transferred onto a polyvinylidene difluoride (PVDF) membrane (RPN 303F, Amersham, Arlington Heights, Ill.). After blocking with a 3% bovine serum albumin solution, the membranes were incubated with a c-Met antibody (Cell Signaling Technology, Danvers, Mass.) overnight at 4° C. A secondary antibody, goat anti-mouse IgG horseradish peroxidase (HRP), was added and the membrane was further incubated for 60 min at room temperature. Finally, the blots were developed using enhanced chemiluminescence (Amersham Pharmacia Biotech, AB, Uppsala, Sweden).

9. Assessment of Cancer Cell Killing Effect

To evaluate the cancer cell killing effect of each viral formulation, A549, MCF7, and HDF cells grown to 70% confluence in 24-well plates were infected with the naked oAd/DCN-shMet, oAd/DCN-shMet/PP, or oAd/DCN-shMet/PPE (A549: 1 MOI, MCF7: 100 MOI, and HDF: 20 MOI). At 2 days post-infection, 200 µL of 3-(4,5-dimethylthiazol-2-yl)-2,5-diphenyl-tetrazolium bromide (MTT; Sigma-Aldrich; 2 mg/mL in PBS) was added to each well and incubated at 37° C. for 4 h. The supernatant was then removed, and the precipitate was dissolved in 1.0 mL of dimethyl sulfoxide (MSO). Plates were read on a microplate reader at 540 nm.

10. Analysis of Innate and Adaptive Immune Responses Against Ad

To determine the acute innate response induced by each Ad formulation, an IL-6 secretion level in mice (n=3) systemically injected with the naked oAd/DCN-shMet, oAd/

DCN-shMet/PP, or oAd/DCN-shMet/PPE was analyzed by enzyme-linked immunosorbant assay (ELISA). Serum samples were collected at 6 h after injection with each oncolytic Ad formulation, and IL-6 levels were then quantified using an IL-6 ELISA kit (R&D Systems, Minneapolis, Minn.).

To analyze the adaptive immune response against the Ad, a single dose of $1\times10^{10}$ VP of the naked oAd/DCN-shMet, oAd/DCN-shMet/PP, or oAd/DCN-shMet/PPE was administered twice on days 0 and 14 by intravenous injection into male BALB/c mice (Charles River Korea Inc., Seoul, Korea). Whole blood was collected from the retro-orbital vein at 14 days after the second injection. Then, mouse serum was incubated at 56° C. for 45 min to inactivate complements, and then stored at −20° C. Neutralization protection assay was performed according to a conventionally known method [46]. In brief, each batch of heat-inactivated serum was diluted 1:50 in serum-free DMEM and then incubated with dAd-GFP (100 MOI) for 20 min at 37° C. A549 cells were transduced with the serum-treated dAd-GFP, and GFP expression was quantitatively analyzed by flow cytometry (BD Biosciences).

11. Analysis of Pharmacokinetic Profile

To assess the rate of Ad clearance from the blood of mice, real-time quantitative PCR (Q-PCR) was performed on whole blood samples from oncolytic Ad-treated mice. The specific method was performed according to a conventionally known method [25, 48]. In brief, 100 µL of whole blood was collected from the retro-orbital plexus of BALB/c mice (n=3) at 5 min, 10 min, 20 min, 30 min, 1 h, 6 h, or 24 h after systemic injection with $1\times10^{10}$ VP of naked oAd/DCN-shMet, oAd/DCN-shMet/PP, or oAd/DCN-shMet/PPE. Total DNA from an aliquot of whole blood was extracted with the QIAamp DNA Blood Mini Kit (Qiagen, Hilden, Germany). The number of Ad genomes was measured by Q-PCR (TaqMan PCR detection; Applied Biosystems, Foster City, Calif.). Samples were analyzed in triplicate and data was processed by the SDS 19.1 software package (Applied Biosystems).

12. In Vivo Antitumor Efficacy and Bioluminescence Imaging Analysis

To compare the antitumor effect of naked oAd/DCN-shMet, oAd/DCN-shMet/PP, and oAd/DCN-shMet/PPE, the orthotopic lung cancer model was established by injecting $1\times10^6$ firefly luciferase-expressing A549 cells into the intrapleural cavity of 6 week-old male nude mice (Charles River Korea Inc.). On day 7 after cell injection, bioluminescence imaging was carried out to confirm the establishment of an orthotopic lung tumor. Mice were anesthetized in a chamber filled with 2% isoflurane in oxygen and received D-luciferin (150 mg/kg; Caliper, Hopkinton, Mass.) by intraperitoneal injection. For the treatment, orthotopic lung tumor-bearing mice (approximately $1\times10^8$ p/s) were randomized into four groups, and intravenously injected three times every other day with 200 µL of PBS, oAd/DCN-shMet, oAd/DCN-shMet PP, or oAd/DCN-shMet/PPE ($2\times10^{10}$ VP).

Both photographic and luminescent images were obtained from the anesthetized mice using the IVIS imaging system (Xenogen, Alameda, Calif.). In vivo bioluminescence signal intensity was obtained as photons acquired per second (photons/second [p/s]) from a body region of interest. Tumor growth was measured every week by bioluminescence imaging following the first treatment. For the evaluation of lung tumors in detail, the lungs of each experimental group were harvested on 3 days after the last treatment with naked oAd/DCN-shMet, oAd/DCN-shMet/PP, or oAd/DCN-shMet/PPE. Each lung of the experimental groups was subsequently incubated in 20 mL of 1×PBS containing 3 mg of D-luciferin (Caliper). Both photographic and luminescent images were obtained by the IVIS imaging system (Xenogen).

13. Histological and Immunohistochemical Analysis

The liver tissues were harvested from mice at 72 h after the last intravenous injection with PBS, naked oAd/DCN-shMet, oAd/DCN-shMet/PP, or oAd/DCN-shMet/PPE. The harvested liver tissues were fixed in 10% formalin, processed for paraffin embedding, and then cut into 5 µm sections. The liver tissue sections were stained with hematoxylin and eosin (H & E), and then examined under an optical microscope. Further, the tumor sections were also immunostained with an Ad E1A-specific antibody (Santa Cruz Biotechnology, Santa Cruz, Calif.) to assess viral replication. The expression levels of Ad E1A were semi-quantitatively assessed by MetaMorph® image analysis software (Universal Image Corp., Buckinghamshire, UK).

14. Biodistribution Assessment by Real-Time Quantitative PCR (Q-PCR)

Once the A549 orthotopic tumor were generated, tumor-bearing mice (n=3) were injected intravenously with $2\times10^{10}$ VP of oAd/DCNshMet, oAd/DCN-shMet/PP, or oAd/DCN-shMet/PPE three times every other day along with PBS as a negative control.

The lung, spleen, kidney, heart, stomach, muscle, liver, and tumor tissues were harvested at 24 h after the third injection of each viral formulation, and DNA was extracted from the tissues using the QIAamp DNA Blood Mini Kit (Qiagen) according to the manufacturer's instructions [26]. The number of viral genomes in each sample was assessed by Q-PCR, as described above.

15. Assessment of In Vivo Toxicity

To measure potential in vivo toxicity of each Ad formulation, mice (n=3) were injected intravenously with $1\times10^{10}$ VP of oAd/DCN-shMet, oAd/DCN-shMet/PP, or oAd/DCN-shMet/PPE along with PBS as a control. Serum levels of aspartate aminotransferase (AST) and alanine transaminase (ALT) were then measured at 3 days post-injection.

16. Statistical Analysis

Data was expressed as the mean±standard deviation (SD). Statistical significance was determined by the two-tailed Student's t-test or one-way ANOVA test (SPSS 13.0 software; SPSS, Chicago, Ill.). P values less than 0.05 were considered statistically significant.

Test Examples

1. Physiochemical Characterization of PP- or PPE-Complexed Ad

In order to prepare an EGFR-targeting and PEGylated PAMAM dendrimer complex (PPE), the inventors generated PEGylated PAMAM (PEG-PAMAM complex, PP) by reacting $PEG_{2.0k}$ (PEG-NHS) with free amine groups of a G4 PAMAM dendrimer (FIG. 1A). Then, the EGFR-specific ErbB antibody (Ab) was conjugated to the remaining amine groups, thus preparing a PEG-PAMAM-ErbB complex (PPE).

Next, the effects of PEGylation and ErbB complexation on PAMAM polymer toxicity were assessed.

As shown in FIG. 1B, PEGylated PAMAM at a concentration of 20 µg/mL or more or 10 µg/mL or more in A549 cells or in MCF7 cells, respectively showed significantly reduced toxicity in comparison to naked PAMAM of the same concentration. This suggests that PEGylation of PAMAM reduced cytotoxicity. Importantly, both PP and PPE demonstrated marginal toxicity up to 100 µg/mL. This implies that both dendrimers are better-suited for in vivo studies in comparison to representative cationic polymers, such as poly(ethylenimine) (PEI) and poly(L-lysine) [35, 36].

To assess the physiochemical attributes of each viral formulation, the average size and surface charge of the dAd-GFP, dAd-GFP/PP, or dAd-GFP/PPE at various molar ratios (Ad:polymer molar ratio; $1\times10^3$, $1\times10^4$, $5\times10^4$, and $1\times10^5$) were analyzed by DLS and Zetasizer 3000HS, respectively.

Figure 1C:
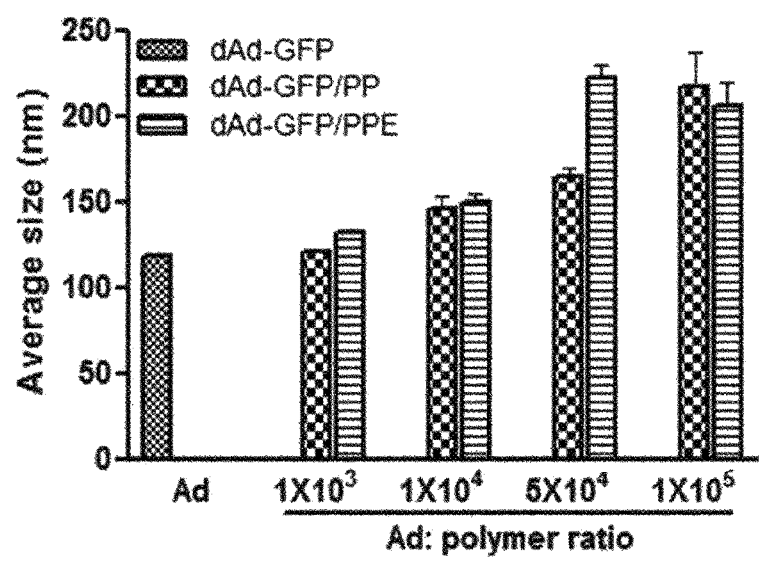
FIG. 1C is a graph showing an average particle size of complexes prepared at various Ad:polymer ratios ($1\times10^3$, $1\times10^4$, $5\times10^4$ and $1\times10^5$) according to an Example of the present invention, the data shows values obtained by performing three independent experiments in triplicate, and bars represent mean±SD.

As shown in FIG. 1C, the average size of naked dAd-GFP was about 117.9±2.0 nm, and complexation with PP or PPE gradually increased the size up to 216.9±19.5 nm or 206.0±13.8 nm, respectively, at an Ad:polymer molar ratio of $1\times10^5$.

Figure 1D:
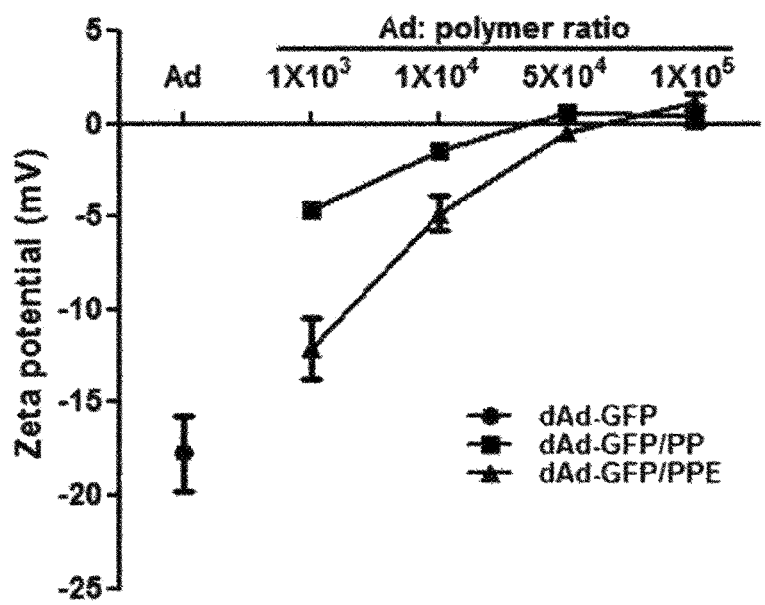
FIG. 1D shows the surface charge of complexes prepared at various Ad: polymer ratios ($1\times10^3$, $1\times10^4$, $5\times10^4$ and $1\times10^5$) according to an Example of the present invention, the data shows values obtained by performing three independent experiments in triplicate, and bars represent mean±SD.

As shown in FIG. 1D, the zeta potential of the particulate's surface was also estimated. The naked Ad had a negative charge of −17.7±2.0 mV, which was attributed to negatively charged amino acids in the capsid proteins of the Ad [50]. The average surface charge increased proportionally to 0.4±0.5 (dAd-GFP/PP) or 1.2±0.4 mV (dAd-GFP/PPE) at a molar ratio of $1\times10^5$. These results suggest that dAd-GFP is well complexed with either dendrimer and a complex's average size is sufficiently small (~200 nm) to be preferentially introduced into the tumor tissues through an enhanced retention and permeability (EPR) effect [50, 51].

Figure 1E:
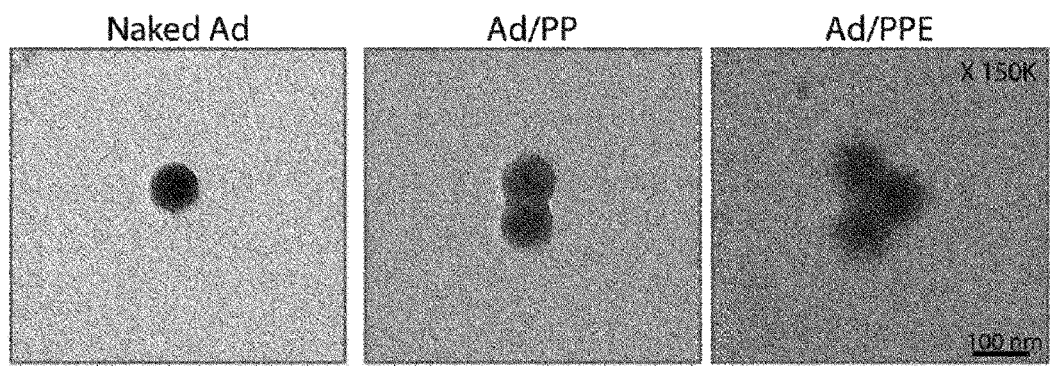
FIG. 1E shows the surface charge of dAd/GFP, dAd/GFP/PP, and dAd/GFP/PPE complexes prepared at a molar ratio of $1\times10^5$ according to an Example of the present invention, the data shows values obtained by performing three independent experiments in triplicate, and bars represent mean±SD.

As shown in FIG. 1E, for morphological characterization of polymer-complexed Ads, transmission electron microscopy (TEM) imaging was performed at a polymer/Ad molar ratio of $1\times10^5$. TEM imaging studies revealed that the naked Ad had a characteristic regular tetrahedral shape. However, in contrast, the dAd-GFP/PP or dAd-GFP/PPE complex had a rough surface structure, suggesting that the Ad particles were completely coated with the polymers. These results clearly demonstrate that the negatively charged Ad was adequately complexed with cationic PP or PPE.

Figure 11:
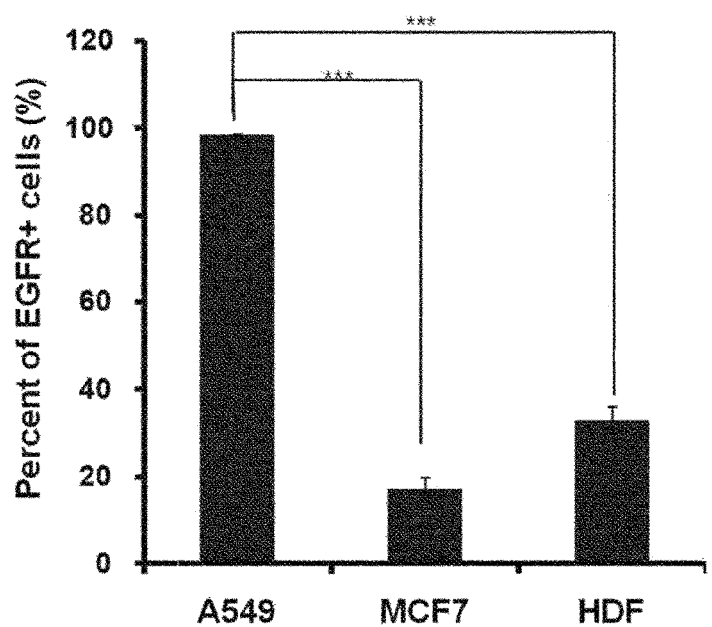
FIG. 11 is a graph showing results identifying the epidermal growth factor receptor (EGFR) expression levels of human cancer cells (A549 and MCF7) and normal cells (HDF), and the values represent mean±SD of three independent experiments.

2. EGFR-Specific Transduction Efficacy of Ad Complexed with ErbB-Conjugated and PEGylated PAMAM Prior to investigating the EGFR-dependent transduction efficiency of dAd-GFP/PPE, the inventors examined the expression levels of EGFR on the surface of various human cancer and normal cells used in this study (cancer: A549 and MCF7; normal: HDF) by flow cytometry. As a result, as shown in FIG. 11, A549 (human lung cancer) showed a high EGFR expression level, whereas MCF7 (human breast cancer cell) and HDF exhibited low EGFR expression.

To assess and optimize transduction efficiency of dAd-GFP/PPE, A549 cancer cells were transduced with dAd-GFP (polyplex) complexed with PP or PPE. A549 cancer cells were transduced at varying molar ratios of the polyplex ($1\times10^3$, $1\times10^4$, $5\times10^4$, $1\times10^5$, and $1\times10^6$), along with naked dAd-GFP as a control.

As shown in FIG. 2, dAd-GFP/PPE exhibited significantly enhanced transduction efficacy in comparison to dAd-GFP/PP in A549 cells ($5\times10^4$ and $1\times10^5$ molar ratios; $P<0.001$). In particular, transduction efficiency of dAd-GFP/PPE was elevated in a PPE dose-dependent manner up to a $1\times10^5$ molar ratio ($P<0.001$), suggesting that PPE complexation on the surface of Ad augmented transduction into EGFR-positive A549 cells. As dAd-GFP/PPE ($1\times10^5$ molar ratio) exhibits a nearly neutral surface charge as demonstrated in FIG. 1D, the increased transduction means that dAd-GFP/PPE complex's entry into cells most likely depends on its targeting moiety ErbB, resulting in selective transduction into EGFR-positive cells.

In particular, as shown in FIGS. 2B and 13, transduction efficacy of dAd-GFP/PPE at a $5\times10^4$ or $1\times10^5$ molar ratio was significantly enhanced over that of naked dAd-GFP. Considering that A549 cells express a high level of CAR, a native receptor for an Ad, it was confirmed that EGFR-mediated transduction of dAd-GFP/PPE seemed to be more efficient than CAR-mediated endocytosis of naked dAd-GFP. In particular, it was confirmed that the EGFR-mediated transduction was significantly excellent in a dAd-GFP/PPE complex having $5\times10^4$ to $1\times10^5$ molar ratios.

To further assess the EGFR-specific transduction efficacy of a PPE-complexed Ad, EGFR-negative cancer cells (MCF7) and normal fibroblast cells (HDF) were treated with naked dAd-GFP, dAd-GFP/PP, or dAd-GFP/PPE. Transduction efficiency of dAd-GFP/PPE at all molar ratios was significantly limited in both MCF7 and HDF cells. These results suggest that transduction of dAd-GFP/PPE most likely relies on the specific interaction between ErbB presented on the surface of dAd-GFP/PPE and EGFR expressed on the cell surface. Since the Ad:PPE molar ratio at $1\times10^5$ showed the highest transduction efficiency of dAd-GFP/PPE in EGFR-positive A549 cells, the $1\times10^5$ molar ratio was selected as an optimal ratio for the preparation of an Ad/PPE complex and utilized in subsequent experiments.

3. Identification of Enhanced Cellular Uptake of PPE-Complexed Ad in EGFR-Overexpressing Cancer Cells To study the link between improved transduction efficiency and intracellular uptake efficiency of the PPE-complexed Ad, EGFR-overexpressing A549 cells were treated with FITC labeled-dAd-GFP, -dAd-GFP/PP, or -dAd-GFP/PPE.

Figure 3A:
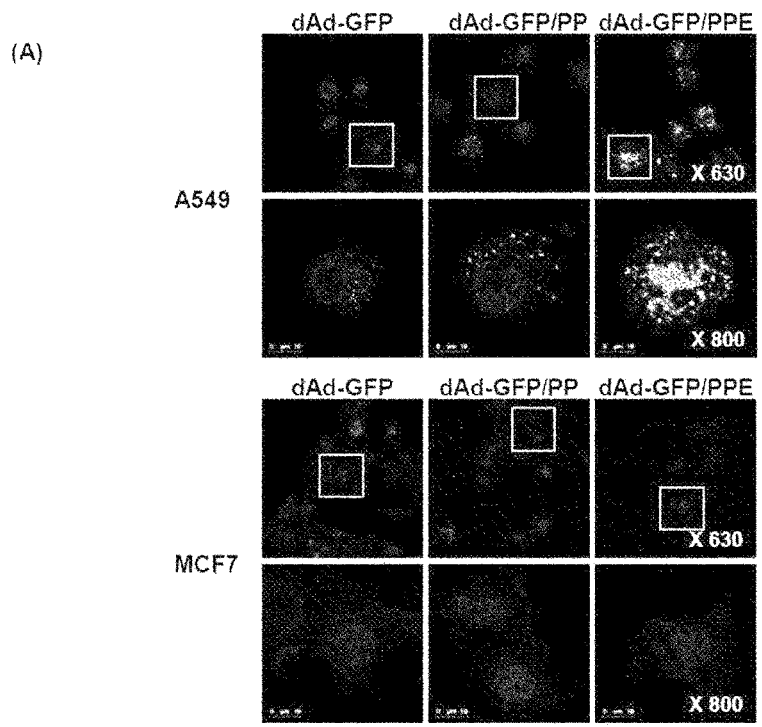
FIG. 3A is a set of confocal laser scanning microscope photographs identifying the cell infiltration ability of dAd-GFP/PPE in EGFR-expressing cancer cells according to an Example of the present invention.
Figure 3B:
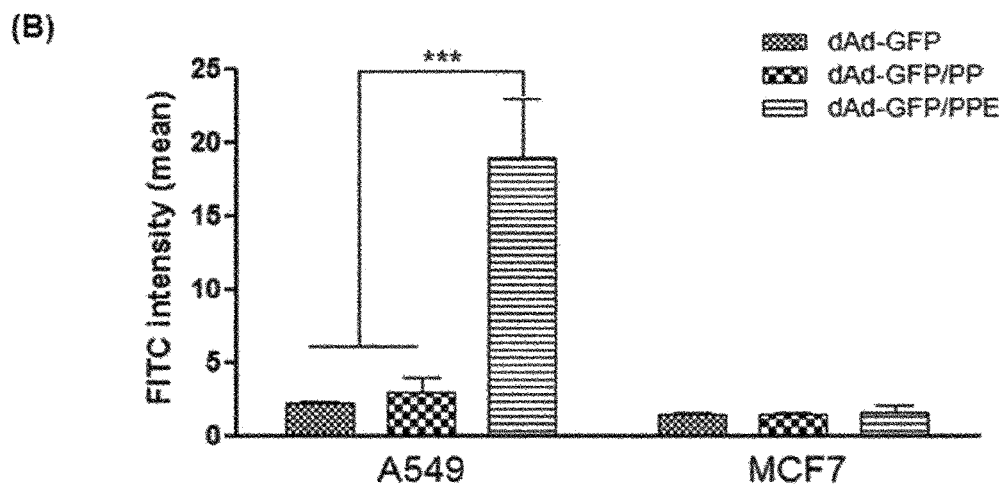
FIG. 3B is a result obtained by analyzing the result identifying the cell infiltration ability of dAd-GFP/PPE in EGFR-expressing cancer cells according to an Example of the present invention with ImageJ image analysis software, the data shows values obtained by performing three independent experiments in triplicate, and bars represent mean±SD (***P<0.001).

As shown in FIGS. 3A and 3B, dAd-GFP/PPE induced 8.6- or 6.5-fold higher intracellular uptake in comparison to either naked dAd-GFP or dAd-GFP/PP at 2 h after treatment with the Ad, respectively, suggesting that efficient intracellular uptake leads to the high transduction efficacy observed in FIG. 2A. In marked contrast, both naked Ad and PP-complexed Ad showed lower green fluorescence compared to dAd-GFP/PPE, suggesting that complexation with PP did not significantly enhance the intracellular uptake of an Ad. dAd-GFP/PP's low intracellular uptake was likely attributed to its neutral surface charge observed in FIG. 1D. Furthermore, it was confirmed that dAd-GFP/PPE was distributed to the nucleus in close proximity, implying that intracellular trafficking was facilitated via more efficient ErbB-mediated intracellular uptake. As expected, no intracellular uptake was observed in EGFR-negative MCF7 cells after treatment with dAd-GFP/PPE, demonstrating the specific ErbB-mediated EGFR-targeting.

4. EGFR-Specific Cellular Entry Mechanism of PPE-Complexed Ad

To examine whether efficient transduction of dAd-GFP/PPE in the EGFR-expressing cancer cells was directly related to EGFR rather than CAR expression, the inventors performed a competition assay with the A549 cell line, which expresses both EGFR and CAR at high levels. To block each receptor on the cell surface, the cells were pretreated with an EGFR- or CAR-specific antibody (Ab) for 1 h [29, 55]. Cells were then transduced with dAd-GFP, dAd-GFP/PP, or dAd-GFP/PPE for 48 h, and GFP expression was assessed by flow cytometry.

As shown in FIG. 4A, dAd-GFP/PPE-mediated GFP expression was significantly reduced when pretreated with the EGFR-specific Ab compared to those without pretreatment with the EGFR-specific Ab (74% reduction; $P<0.001$), whereas no apparent reduction was observed in dAd-GFP/PP-treated cells even after treatment with the EGFR-specific antibody (Ab).

To further assess whether the cellular entry mechanism of dAd-GFP/PPE differs from CAR-mediated endocytosis of the naked Ad, A549 cells were pre-incubated with a CAR-specific antibody (Ab) to block the viral entry via CAR. As demonstrated in FIG. 4B, pre-treatment of the CAR-specific antibody (Ab) noticeably attenuated GFP expression of the naked Ad by 92% (P<0.001) compared to that of the untreated naked Ad. In contrast, both dAd-GFP/PP and dAd-GFP/PPE induced only 6% and 34% decreases in GFP expression, respectively, indicating that blockage of CAR-mediated entry did not markedly affect the entry of dendrimer-coated Ads due to masking by PP or PPE. These results demonstrate that dAd-GFP/PPE is mainly internalized into the cells by the specific interaction between EGFR on the surface of cells and ErbB displayed on the surface of PPE.

5. Preparation and Characterization of Oncolytic Ad Co-Expressing DCN and shMet

Figure 12A:
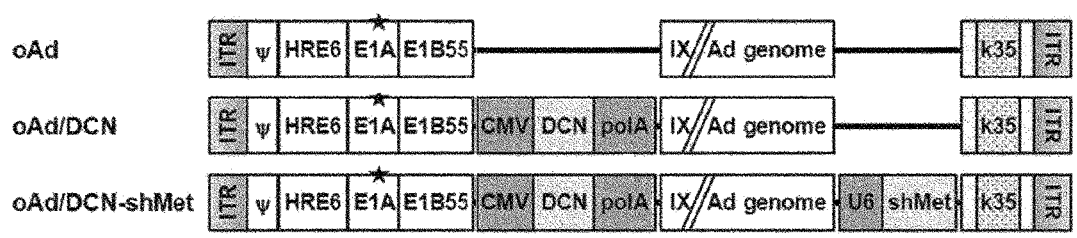
FIG. 12A shows the structures of an oncolytic Ad co-expressing DCN and shMet.

Abnormally elevated RTK signaling has been identified as an oncogenic factor of lung cancer development, thus many studies have been attempted to develop new drugs that specifically target RTK signaling [3-5]. DCN can bind and down-regulate several RTKs, such as EGFR [37, 38] and the insulin-like growth factor receptor type I [56]. Beside, DCN antagonizes the c-Met proto-oncogene by cleavage of its extracellular domain [57]. The inventors have recently reported that an oncolytic Ad expressing shMet leads to the suppression of RTK signaling-induced cancer cell proliferation and tumor growth. In order to evaluate combined therapeutic efficacy of these two therapeutic genes for lung cancer treatment, the inventors have prepared an oncolytic Ad co-expressing DCN and shMet (oAd/DCN-shMet) which replicates more efficiently under hypoxic conditions, a hallmark of tumor tissue (FIG. 12A)[55].

Figure 12B:
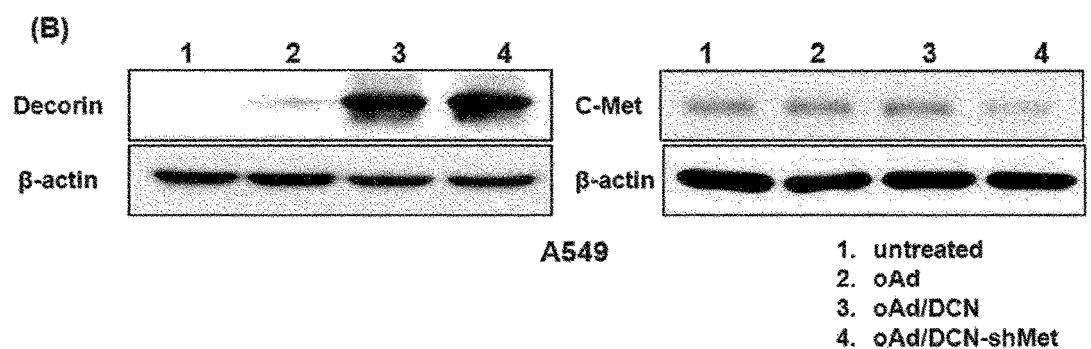
FIG. 12B shows results identifying the expression levels of DCN and c-Met in A549 cells via a Western blot.
Figure 12C:
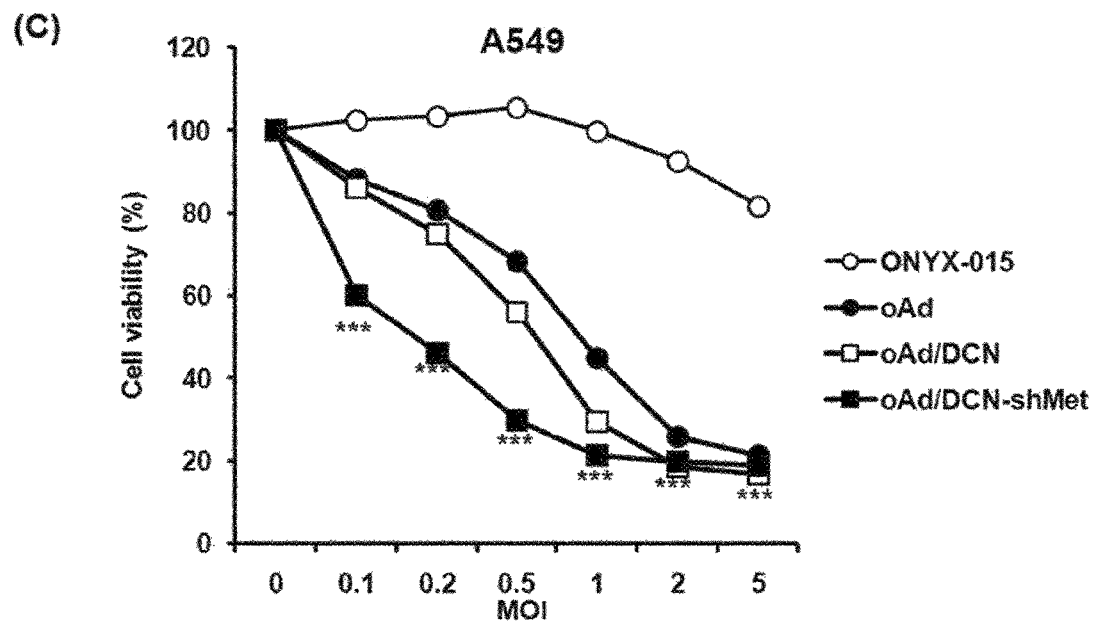
FIG. 12C is a result identifying the cell killing ability of an oncolytic Ad according to an Example of the present invention.
Figure 12D:
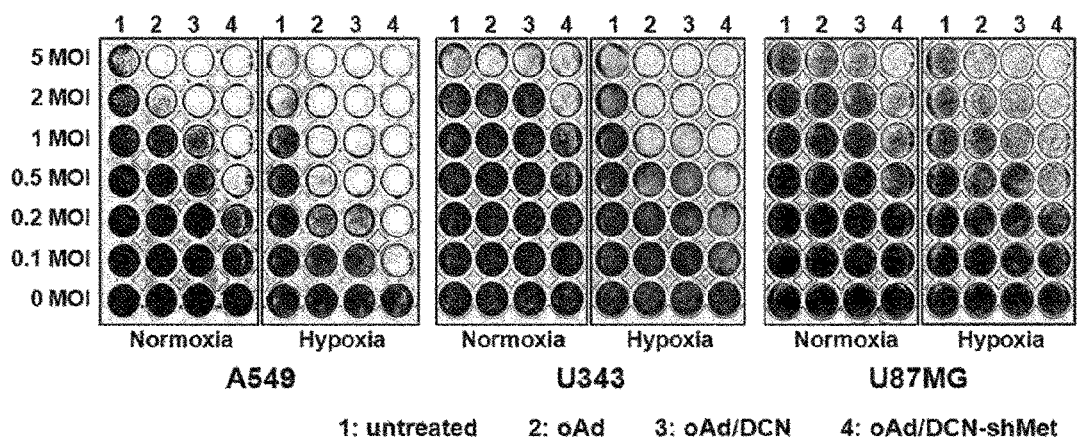
FIG. 12D shows results identifying cancer cell killing effects of oncolytic Ad under hypoxic conditions and normoxic conditions.

To assess whether the newly prepared oncolytic Ad could express DCN and suppress c-Met efficiently, the expression levels of DCN and c-Met were investigated via Western blot analysis (FIG. 12B). oAd/DCNshMet exhibited greater DCN expression and significantly decreased c-Met expression than either untreated cells or the control oncolytic Ad. This indicates that oAd/DCN-shMet was well constructed and expresses transgenes properly. Further, oAd/DCN-shMet expressed a markedly greater cancer cell killing effect compared with the control oncolytic Ad (oAd) or the DCN-expressing oncolytic Ad (oAd/DCN) up to 1 MOI (***P<0.001; FIG. 12C). This suggests that shMet expression can enhance a cancer-specific cytopathic effect of the oncolytic Ad. Importantly, the oAd showed much more potent cancer cell killing efficacy than a commercialized oncolytic Ad (ONYX-015; comparable to Oncorine™). To assess the effect of HRE on viral replication under hypoxic conditions, the inventors have treated various cancer cells with oAd/DCN or oAd/DCN-shMet under hypoxic or normoxic conditions, along with the control oAd. As shown in FIG. 12D, oAd/DCN-shMet induced more potent cancer cell killing efficacy under hypoxic conditions than normoxic conditions. This finding is in good agreement with our previous reports where HRE-incorporated oncolytic Ads demonstrated a potent and selective cancer cell killing effect due to enhanced viral replication under the hypoxic state of the tumor [58].

Figure 5A:
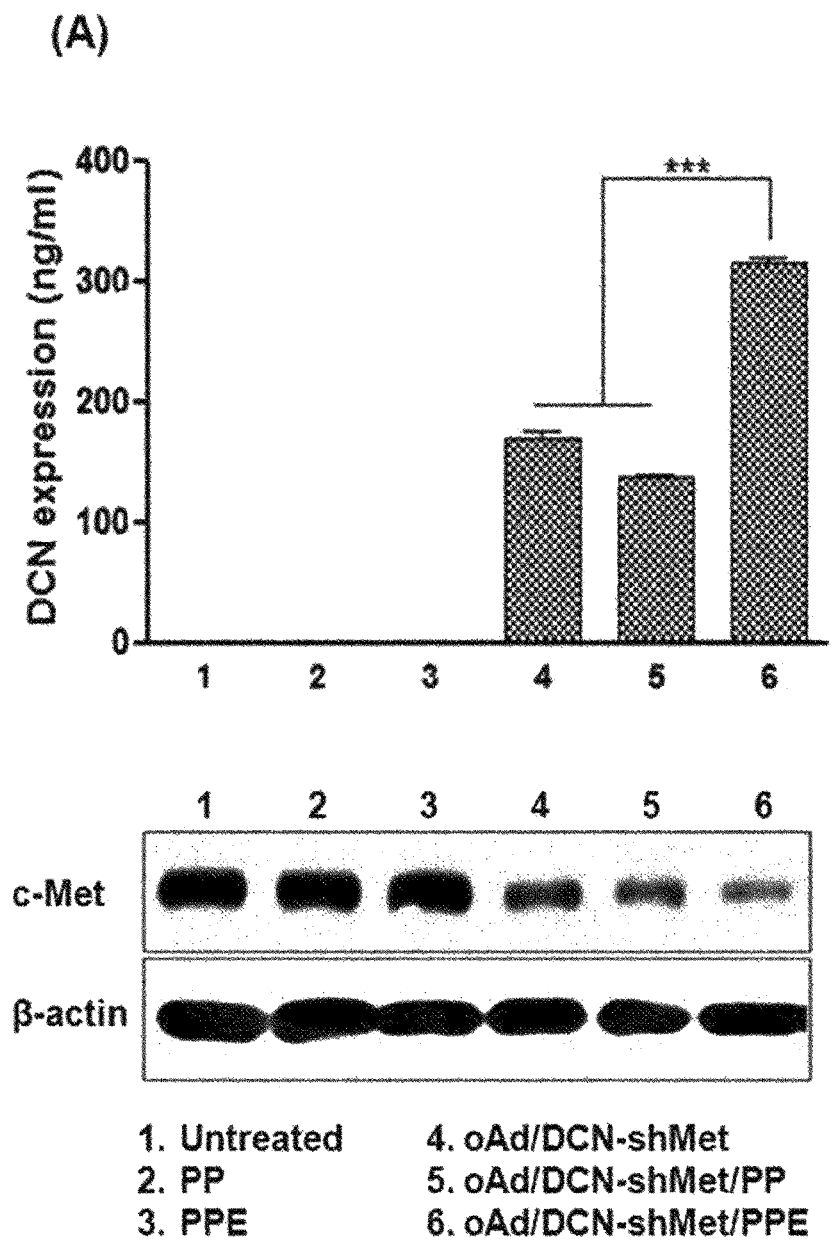
FIG. 5A is a graph showing results identifying enhanced gene expression (expression of DCN and c-Met) of complexes according to an Example of the present invention, the data shows values obtained by performing three independent experiments in triplicate, and bars represent mean±SD (***P<0.001).

To investigate whether the therapeutic potential of oAd/DCN-shMet can be further improved by complexation with PPE, oncolytic Ad-mediated DCN and c-Met expression levels were determined by ELISA and Western blot analysis, respectively. As shown in FIG. 5A, markedly enhanced DCN expression and significant suppression of c-Met expression were observed in oAd/DCN-shMet/PPE-treated cells when compared with either naked oAd/DCN-shMet or oAd/DCN-shMet/PP, indicating that oncolytic Ad-mediated transgenes are more efficiently expressed when the Ad was introduced into cells with PPE. These results are consistent with our transduction efficiency results shown in FIG. 2.

To assess EGFR-dependent cancer cell killing efficacy, EGFR-high (A549) and -low (MCF7 or HDF) expressing cells were treated with PP, PPE, naked oAd/DCN-shMet, oAd/DCN-shMet/PP, or oAd/DCNshMet/PPE.

Figure 5B:
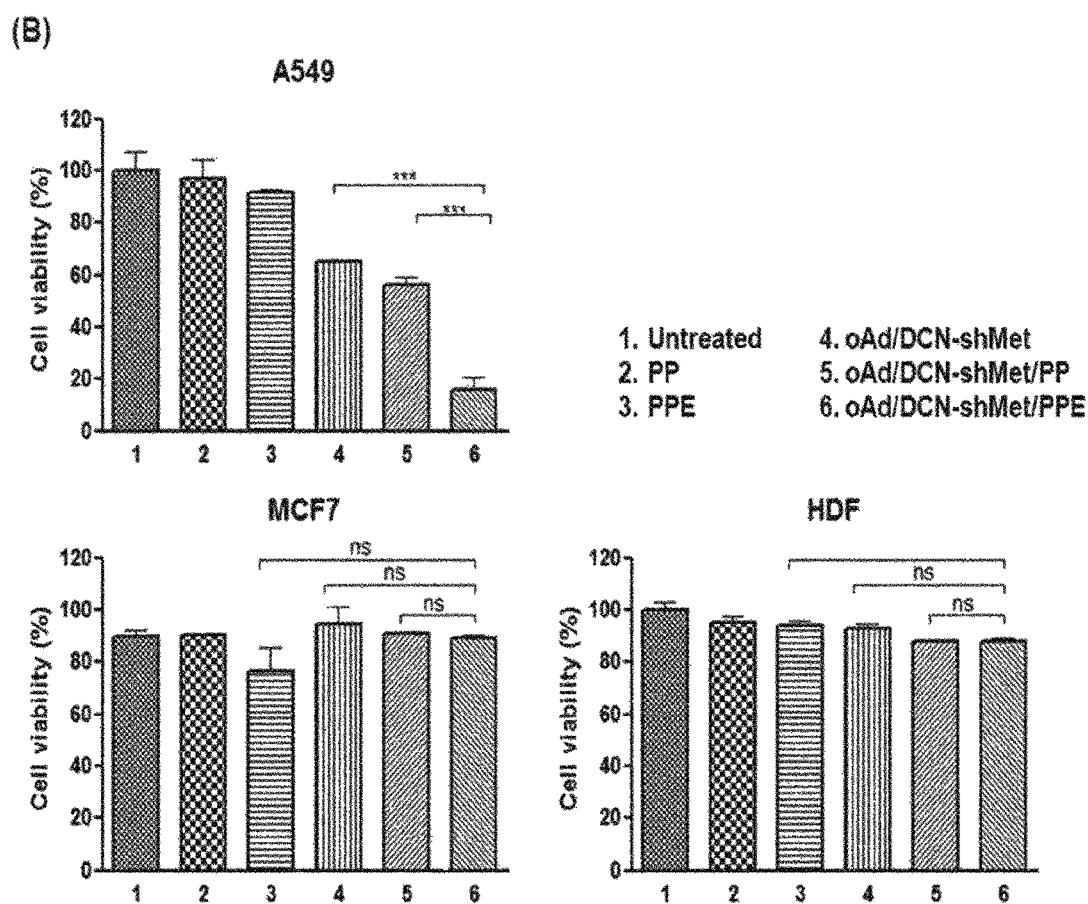
FIG. 5B is a graph showing results identifying an EGFR-specific cancer cell killing effect of complexes according to an Example of the present invention, the data shows values obtained by performing three independent experiments in triplicate, and bars represent mean±SD (***P<0.001).

As shown in FIG. 5B, coating the surface of oAd/DCN-shMet with PPE significantly increased A549 cancer cell killing efficacy up to 2.5-fold in comparison to naked oAd/DCN-shMet (P<0.001), implying that PPE complexation can enhance the therapeutic potency of an oncolytic Ad to treat EGFR-overexpressing cancer. In marked contrast, no apparent cell killing was observed in oAd/DCN-shMet/PPE-treated MCF7 and HDF cells. Taken together, these results demonstrate that oAd/DCN-shMet/PPE can markedly enhance cancer cell killing efficacy in EGFR-expressing cancer cells, while protecting non-targeted cells from the cytolytic activity of an oncolytic Ad.

6. Identification of Effect of Attenuating Ad-Associated Innate and Adaptive Immune Responses by PPE-Complexed Oncolytic Ad Innate and adaptive immune responses induced by the immunogenicity of an Ad viral capsid are a critical hurdle to systemic administration of Ad vectors. An intravenously administered Ad is rapidly inactivated and cleared by the activation of the host's antiviral immunity, thus limiting the therapeutic efficacy of an Ad [59, 60]. In order to assess whether complexation with PPE could reduce the immunogenicity of an oncolytic Ad, innate and adaptive immune responses against systemically administered naked oAd/DCN-shMet, oAd/DCN-shMet/PP, or oAd/DCN-shMet/PPE were analyzed.

Figure 6A:
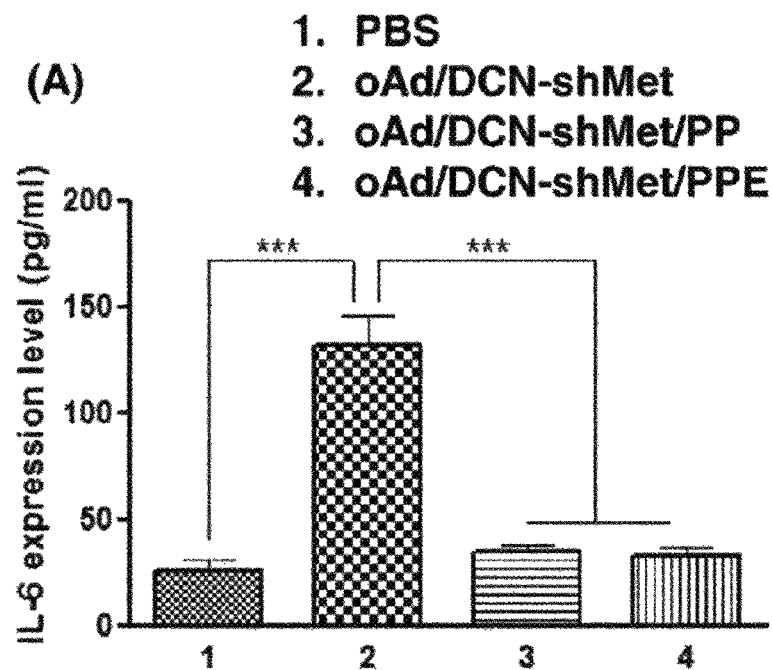
FIG. 6A is a graph showing an effect of attenuating Ad-associated innate immune responses of complexes according to an Example of the present invention, the data shows values obtained by performing three independent experiments in triplicate, and bars represent mean±SD (***P<0.001).

As shown in FIG. 6A, systemically injected naked oAd/DCN-shMet led to strong induction of IL-6 production (131.9 pg/mL) which was 5.1-fold higher than that of PBS-treated control mice (25.7 pg/mL, P<0.001). In contrast, both oAd/DCN-shMet/PP and oAd/DCN-shMet/PPE did not alter basal levels of IL-6 secretion (34.8 and 32.9 pg/mL, respectively). These results are likely due to the effect of PEGylated PAMAM on the surface of an Ad which shields against recognition by innate immune response mediators such as monocytes or macrophages [61]. The IL-6 expression levels of oAd/DCN-shMet/PP and oAd/DCN-shMet/PPE were not significantly different, indicating that ErbB conjugation to PP did not negatively affect the shielding effect by PP.

The inventors further examined whether oAd/DCN-shMet/PPE could overcome rapid clearance induced by an Ad-specific neutralizing Ab which is integral to the adaptive immune response.

Figure 6B:
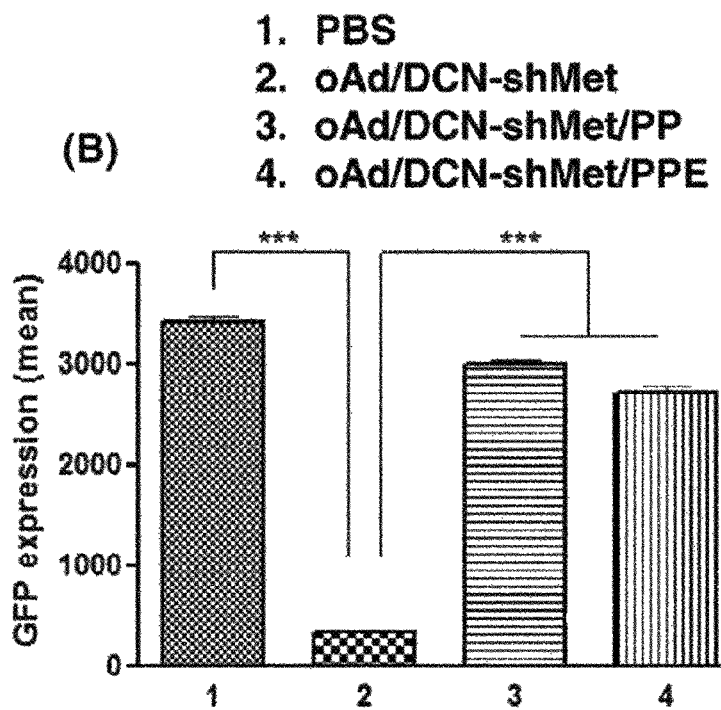
FIG. 6B is a graph showing an effect of attenuating Ad-associated adaptive immune responses of complexes according to an Example of the present invention, the data shows values obtained by performing three independent experiments in triplicate, and bars represent mean±SD (***P<0.001).

As shown in FIG. 6B, an Ad-specific antibody (Ab)-containing serum from mice treated with a naked oncolytic Ad reduced dAd-GFP-mediated GFP expression in A549 cells by 90% compared to those treated with serum from PBS-administered mice (P<0.001). In contrast, dAd-GFP-mediated GFP expression in the presence of serum from mice injected with oAd/DCN-shMet/PP or oAd/DCN-shMet/PPE was only reduced by 12.5% and 20.4%, respectively, showing that both dendrimer-coated oncolytic Ads can efficiently evade induction of the adaptive immune response against an Ad. Since a neutralizing Ab inactivates an Ad and causes the failure of repeated administration of Ad vectors, this strong reduction in Ad-specific neutralizing Ab production could increase the utility of oAd/DCN-shMet/PPE for multiple injections through systemic administration. These results demonstrate that oAd/DCN-shMet/PPE can efficiently attenuate both Ad-associated innate and adaptive immune responses.

7. Improved Pharmacokinetic Profile of PPE-Complexed Oncolytic Ad

For the efficient treatment of disseminated cancer cells in the lungs by systemic injection, blood retention time of an Ad must be prolonged to deliver the majority of the oncolytic Ad to targeted tumor tissues [62, 63]. As oncolytic Ad-mediated innate and adaptive immune responses are associated with rapid blood clearance of systemically administered oncolytic Ad, the inventors assessed whether significantly attenuated immunogenicity of a dendrimer-coated oncolytic Ad could translate into prolonged blood retention time of the oncolytic Ad.

Figure 7:
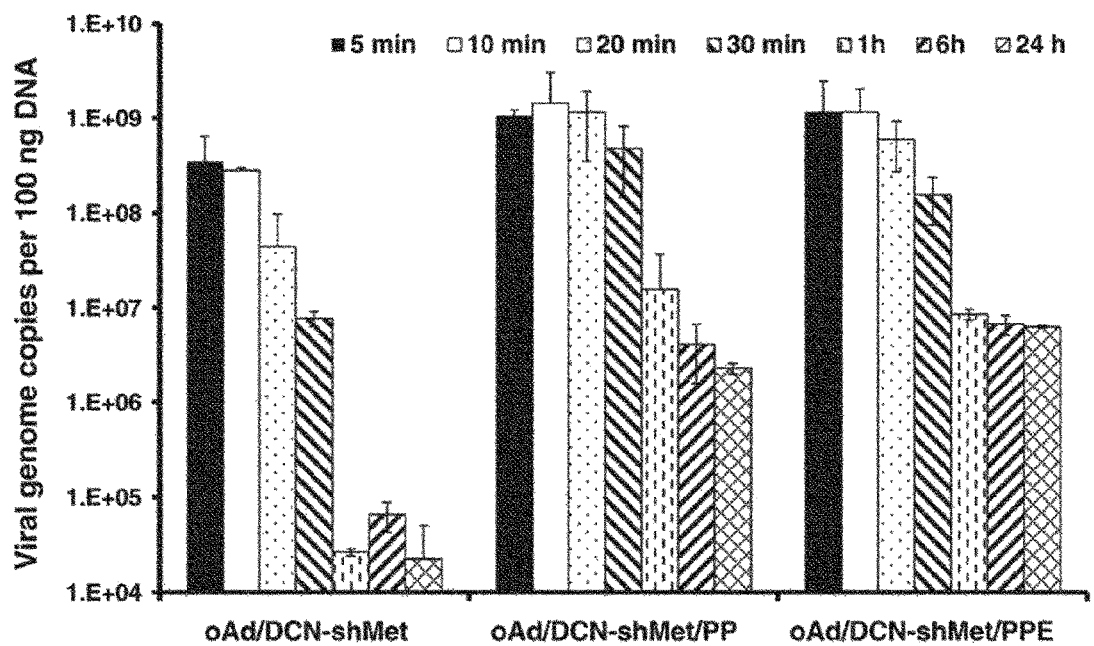
FIG. 7 is a graph showing improved pharmacokinetic profiles of complexes according to an Example of the present invention, the data shows values obtained by performing three independent experiments in triplicate, and bars represent mean±SD.

As shown in FIG. 7, naked oAd/DCN-shMet was rapidly cleared from blood with only 2.8% of the initial infusion dose remaining at 10 min post-injection. In contrast, oAd/DCN-shMet/PP and oAd/DCN-shMet/PPE maintained 3.0- and 3.3-fold higher levels than naked oAd/DCN-shMet, respectively ($P<0.001$). Of note, naked oAd/DCN-shMet was almost completely cleared from the blood by 1 h post-injection, whereas the oncolytic Ad complexed with PP or PPE was retained at 600- or 330-fold higher levels than naked oAd/DCN-shMet ($P<0.001$). At 24 h after injection, 100- or 290-fold higher levels of oAd/DCN-shMet/PP and oAd/DCN-shMet/PPE were still remaining in blood circulation compared to naked oAd, demonstrating that the PPE-coated oncolytic Ad can efficiently mask the Ad surface which reduces the immunogenicity of a systemically administered oncolytic Ad while further enhancing blood circulation time.

8. Potent Therapeutic Efficacy of oAd/DCN-shMet/PPE in an Orthotopic Lung Cancer Model Solid tumors inaccessible by a needle, such as lung, liver, and pancreatic cancer, cannot be treated by intratumoral administration and require systemic treatment. In order to properly evaluate the therapeutic effect of each systemically administered oncolytic Ad regimen, luciferase-expressing orthotopic lung tumors were treated with oAd/DCN-shMet, oAd/DCNshMet/PP, or oAd/DCN-shMet/PPE via tail-vein injection.

Figure 8A:
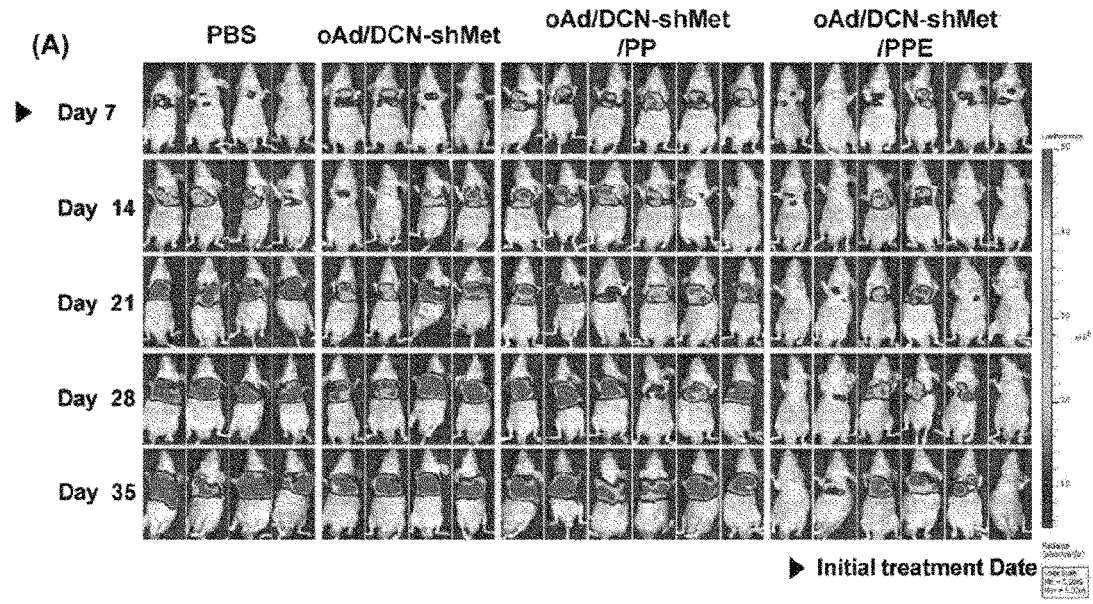
FIGS. 8A and 8B are photographs (8A) and a graph (8B) showing potent antitumor effects in an orthotopic model of complexes according to an Example of the present invention, the data shows values obtained by performing three independent experiments in triplicate, and bars represent mean±SD (*P<0.05).
Figure 8B:
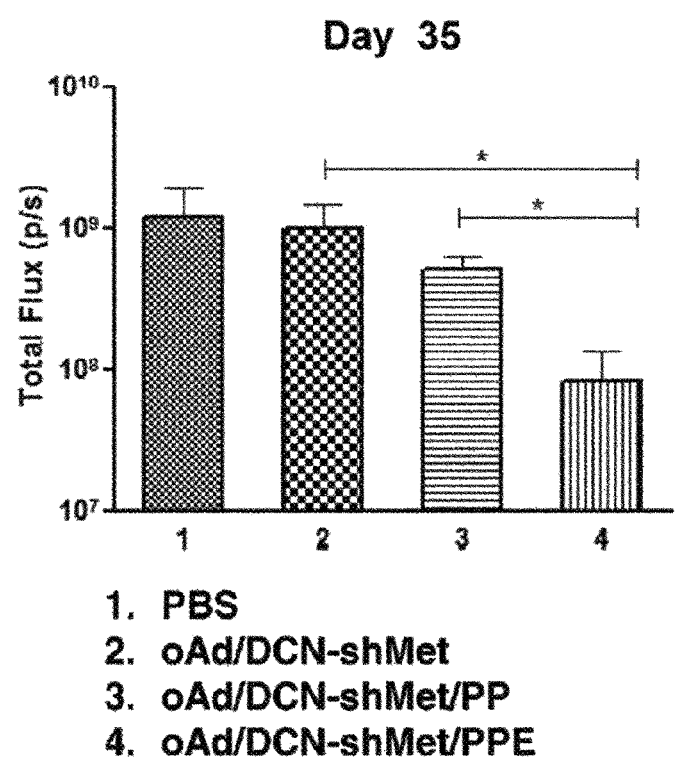

As shown in FIGS. 8A and 8B, systemic administration of oAd/DCN-shMet/PPE resulted in markedly higher antitumor activity than either naked oAd/DCN-shMet or oAd/DCN-shMet/PP. At 35 days post-injection, the luciferase signal from the orthotopic lung tumors of mice treated with oAd/DCN-shMet/PPE ($8.2 \times 10^7$ $5.1 \times 10^7$ p/s) was significantly attenuated in comparison to other groups ($P<0.05$), demonstrating 14.9-, 7.7-, or 6.3-fold greater therapeutic efficacy than PBS ($1.2 \times 10^9 \pm 7.5 \times 10^8$ p/s), naked oAd/DCN-shMet ($6.3 \times 10^8 \pm 1.4 \times 10^8$ p/s), or oAd/DCN-shMet/PP ($5.1 \times 10^8 \pm 1.1 \times 10^8$ p/s), respectively.

Figure 14:
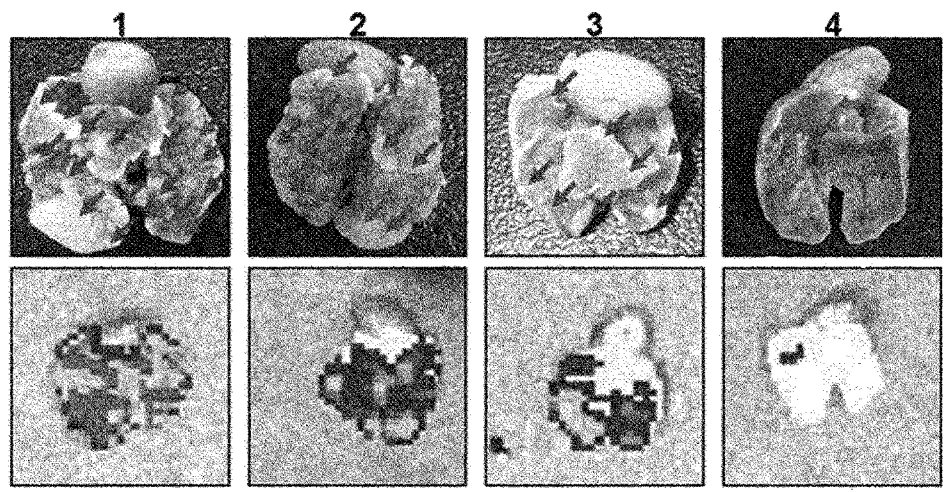
FIG. 14 is a set of ex vivo photographs of lungs identifying changes in size of a tumor by treatment with complexes according to an Example of the present invention.

As shown in FIG. 14, ex vivo imaging of the lungs further supports these results that naked oAd/DCN-shMet- and oAd/DCN-shMet/PP-treated lungs had a high tumor burden, whereas oAd/DCN-shMet/PPE-treated tumors had evidently a lower tumor burden. This potent therapeutic efficacy of oAd/DCN-shMet/PPE following systemic administration might be attributed to enhanced blood retention time, a highly efficient EGFR-targeting ability, and a potent cell killing effect of oAd/DCN-shMet against lung cancer.

To further investigate the therapeutic effect and the replication degree of an oncolytic Ad, tumor tissues were harvested at 3 days after the last treatment with each group (PBS, oAd/DCN-shMet, oAd/DCNshMet/PP, or oAd/DCN-shMet/PPE).

Figure 8C:
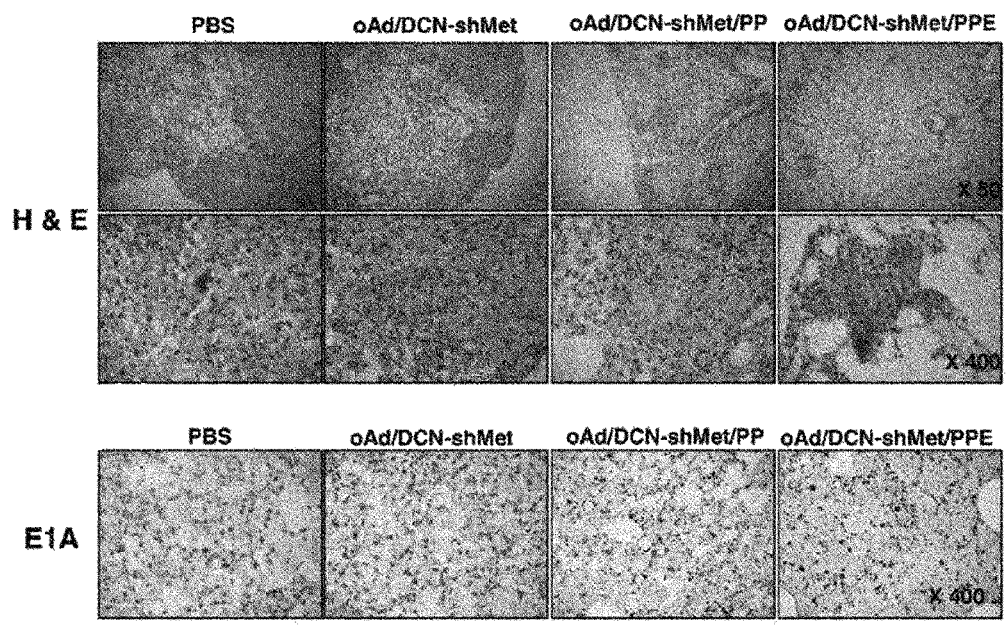
FIGS. 8C and 8D are graphs (8C) and a graph (8D) identifying antitumor effects of complexes according to an Example of the present invention, the data shows values obtained by performing three independent experiments in triplicate, and bars represent mean±SD (***P<0.001).
Figure 8D:
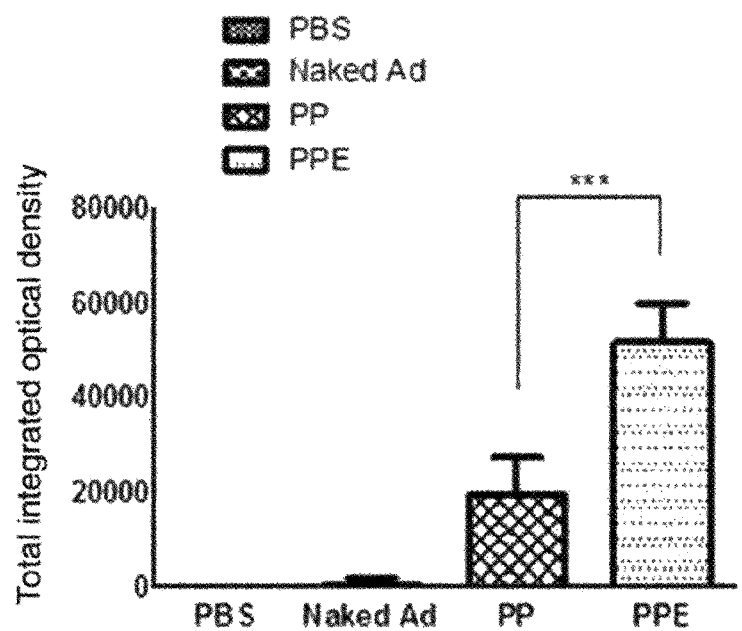

As shown in FIGS. 8C and 8D, H & E staining revealed large areas of proliferating tumor cells in either PBS- or naked oAd/DCN-shMet-treated tissues. Further, oAd/DCN-shMet/PP-treated tumor tissues showed moderate areas of proliferating tumor cells. In marked contrast, oAd/DCN-shMet/PPE-treated tumor tissues exhibited a markedly lower level of proliferating tumor cells compared with PBS-, oAd/DCN-shMet-, or oAd/DCN-shMet/PP-treated tissues. Moreover, tumor tissues treated with oAd/DCN-shMet/PP or oAd/DCN-shMet/PPE showed 33.2- or 88.6-fold higher Ad E1A expression than those treated with naked oAd/DCN-shMet. Of note, oAd/DCN-shMet/PPE-treated tumor tissues exhibited 2.7-fold higher Ad E1A expression than oAd/DCN-shMet/PP, implying that ErbB-conjugated PPE can enhance the intratumoral accumulation of an Ad in EGFR-expressing tumors ($P<0.001$).

9. Enhanced Therapeutic and Safety Profile of oAd/DCN-shMet/PPE

A naked Ad is rapidly and nonspecifically sequestered in the liver following intravenous injection due to interactions with Kupffer cells and coagulation factors, resulting in hepatotoxicity and a limited antitumor effect. To further examine whether PPE-coating can prevent nonspecific liver uptake and enhance intratumoral accumulation of an oncolytic Ad, the biodistribution of systemically administered naked oAd/DCN-shMet, oAd/DCN-shMet/PP, or oAd/DCN-shMet/PPE was analyzed in nude mice bearing orthotopic lung tumors.

Figure 9A:
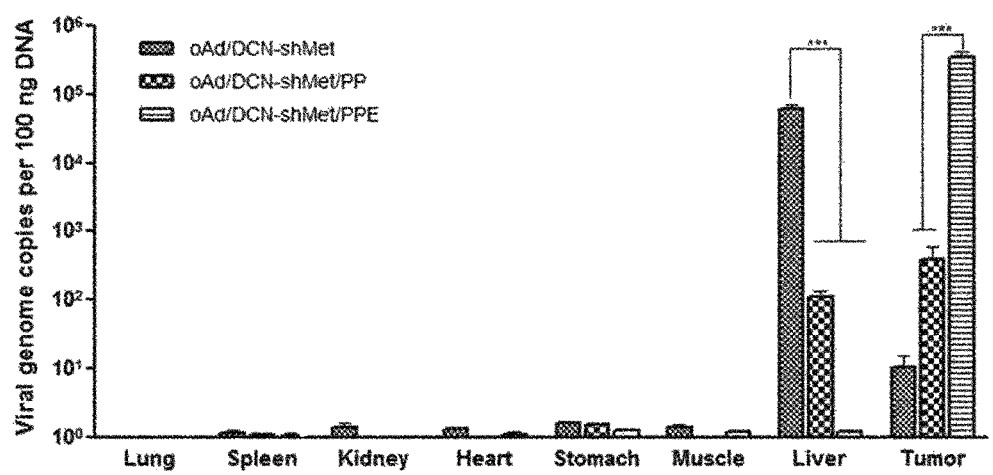
FIG. 9A is a result identifying the biodistribution of complexes according to an Example of the present invention after systemic administration, the data shows values obtained by performing three independent experiments in triplicate, and bars represent mean±SD (***P<0.001).

As shown in FIG. 9A, the liver uptakes of oAd/DCN-shMet/PP and oAd/DCN-shMet/PPE were significantly reduced in comparison to that of naked oAd/DCN-shMet, exhibiting 550- and 52,000-fold less accumulation, respectively ($P<0.001$). In marked contrast, oAd/DCN-shMet/PP or oAd/DCN-shMet/PPE showed 38- or 33,000-fold higher accumulation in the tumor than naked oAd/DCN-shMet, respectively ($P<0.001$). In particular, oAd/DCN-shMet/PPE showed the highest tumor targeting ability eliciting 870-fold higher accumulation in the tumor tissues than oAd/DCN-shMet/PP, implying that the ErbB-EGFR interaction can lead to efficient internalization of an oncolytic Ad. These results are consistent with augmented cellular uptake of Ad/PPE in EGFR-positive cells in comparison to either a naked Ad or Ad/PP. Once oAd/DCN-shMet/PPE is effectively internalized into EGFR-positive cancer cells, an oncolytic Ad can selectively-replicate and infect adjacent cancer cells, further contributing to a significant difference in viral accumulation observed only in the tumor tissue [19, 20]. Further, these results are in agreement with FIGS. 8C and 8D, which demonstrated markedly increased localization of an Ad in the tumor tissues treated with oAd/DCN-shMet/PPE than that with oAd/DCN-shMet/PP. Consequently, the tumor-to-liver ratio of oAd/DCN-shMet/PPE was $1.7 \times 10^9$-fold greater than that of naked oAd/DCN-shMet. These results imply that the increased tumor accumulation and decreased liver sequestration of oAd/DCN-shMet/PPE lead to an enhanced therapeutic outcome.

Next, hepatotoxicity was analyzed with ALT and AST levels after systemic administration of naked oAd/DCN-shMet, oAd/DCN-shMet/PP, or oAd/DCN-shMet/PPE.

Figure 9B:
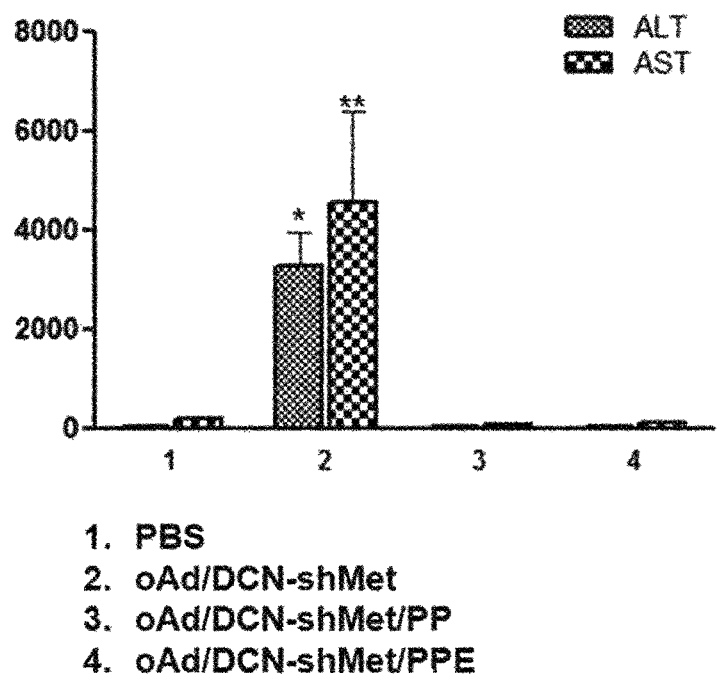
FIGS. 9B and 9C are a graph (9B) and photographs (9C) showing results identifying reduced toxicity and increased tumor accumulation of complexes according to an Example of the present invention after systemic administration, the data shows values obtained by performing three independent experiments in triplicate, and bars represent mean±SD (***P<0.001).

As shown in FIG. 9B, mice treated with naked oAd/DCN-shMet showed the highest ALT and AST levels (78.9- and 24.3-fold higher than the PBS-treated group; $P>0.05$, $P>0.01$, respectively). In contrast, no significant increase in ALT and AST levels were observed in mice treated with oAd/DCN-shMet/PP or oAd/DCN-shMet/PPE, demonstrating that systemically delivered Ad-related hepatic damage can be markedly attenuated with PP or PPE complexation.

Figure 9C:
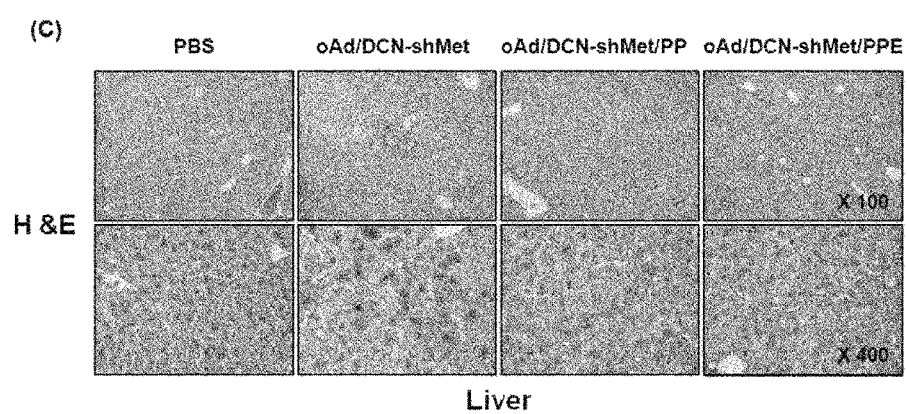

Further, as shown in FIG. 9C, acidophilic necrosis-induced formation of a Councilman body and nuclei degeneration (mitosis or dinuclear), which are hallmarks of hepatic damage, were observed in the naked Ad-treated mice. Conversely, no hepatic damage-related morphological abnormalities were detected in mice treated with oAd/DCN-shMet/PP or oAd/DCN-shMet/PPE, demonstrating that dendrimer-coating over the surface of oAd/DCN-shMet can reduce Ad-associated hepatotoxicity.

Altogether, the present invention demonstrates that coating the surface of oAd/DCN-shMet with PPE can overcome well-known impediments against systemic administration of an oncolytic Ad, such as immunogenicity (FIGS. 6A and 6B), short blood circulation time (FIG. 7), nonspecific liver entry, and hepatotoxicity, and enhance tumor targeting (FIG. 9A) and therapeutic potency (FIGS. 8A, 8B, 8C, and 8D).

REFERENCE

[1] R. Siegel, J. Ma, Z. Zou, A. Jemal, Cancer statistics, 2014, CA Cancer J. Clin. 64 (2014) 9-29.
[2] B. K. Edwards, A. M. Noone, A. B. Mariotto, E. P. Simard, F. P. Boscoe, S. J. Henley, A. Jemal, H. Cho, R. N. Anderson, B. A. Kohler, C. R. Eheman, E. M. Ward, Annual report to the nation on the status of cancer, 1975-2010, featuring prevalence of comorbidity and impact on survival among persons with lung, colorectal, breast, or prostate cancer, Cancer 120 (2014) 1290-1314.
[3] A. B. Sandler, D. H. Johnson, R. S. Herbst, Anti-vascular endothelial growth factor monoclonals in non-small cell lung cancer, Clin. Cancer Res. 10 (2004) 4258s-4262s.
[4] G. Giaccone, Epidermal growth factor receptor inhibitors in the treatment of nonsmall-cell lung cancer, J. Clin. Oncol. 23 (2005) 3235-3242.
[5] B. Besse, A. Adjei, P. Baas, P. Meldgaard, M. Nicolson, L. Paz-Ares, M. Reck, E. F. Smit, K. Syrigos, R. Stahel, E. Felip, S. Peters, M. Panel, 2nd ESMO Consensus Conference on Lung Cancer: non-small-cell lung cancer first-line/second and further lines of treatment in advanced disease, Ann. Oncol. 25 (2014) 1475-1484.
[6] Y. Ohsaki, S. Tanno, Y. Fujita, E. Toyoshima, S Fujiuchi, Y. Nishigaki, S. Ishida, A. Nagase, N. Miyokawa, S. Hirata, K. Kikuchi, Epidermal growth factor receptor expression correlates with poor prognosis in non-small cell lung cancer patients with p53 overexpression, Oncol. Rep. 7 (2000) 603-607.
[7] K. Inamura, H. Ninomiya, Y. Ishikawa, O. Matsubara, Is the epidermal growth factor receptor status in lung cancers reflected in clinicopathologic features? Arch. Pathol. Lab. Med. 134 (2010) 66-72.
[8] N. E. Hynes, H. A. Lane, ERBB receptors and cancer: the complexity of targeted inhibitors, Nat. Rev. Cancer 5 (2005) 341-354.
[9] V. Beljanski, J. Hiscott, The use of oncolytic viruses to overcome lung cancer drug resistance, Curr. Opin. Virol. 2 (2012) 629-635.
[10] D. Irmer, J. O. Funk, A. Blaukat, EGFR kinase domain mutations—functional impact and relevance for lung cancer therapy, Oncogene 26 (2007) 5693-5701.
[11] A. Okines, D. Cunningham, I. Chau, Targeting the human EGFR family in esophagogastric cancer, Nat. Rev. Clin. Oncol. 8 (2011) 492-503.
[12] F. Dong, L. Wang, J. J. Davis, W. Hu, L. Zhang, W. Guo, F. Teraishi, L. Ji, B. Fang, Eliminating established tumor in nu/nu nude mice by a tumor necrosis factor-alpharelated apoptosis-inducing ligand-armed oncolytic adenovirus, Clin. Cancer Res. 12 (2006) 5224-5230.
[13] V. Rusch, D. Klimstra, E. Venkatraman, P. W. Pisters, J. Langenfeld, E. Dmitrovsky, Overexpression of the epidermal growth factor receptor and its ligand transforming growth factor alpha is frequent in resectable non-small cell lung cancer but does not predict tumor progression, Clin. Cancer Res. 3 (1997) 515-522.
[14] G. Fontanini, M. De Laurentiis, S. Vignati, S. Chine, M. Lucchi, V. Silvestri, A. Mussi, S. De Placido, G. Tortora, A. R. Bianco, W. Gullick, C. A. Angeletti, G. Bevilacqua, F. Ciardiello, Evaluation of epidermal growth factor-related growth factors and receptors and of neoangiogenesis in completely resected stage I-IIIA non-small-cell lung cancer: amphiregulin and microvessel count are independent prognostic indicators of survival, Clin. Cancer Res. 4 (1998) 241-249.
[15] D. Raben, B. Helfrich, D. C. Chan, F. Ciardiello, L. Zhao, W. Franklin, A. E. Baron, C. Zeng, T. K. Johnson, P. A. Bunn Jr., The effects of cetuximab alone and in combination with radiation and/or chemotherapy in lung cancer, Clin. Cancer Res. 11 (2005) 795-805.
[16] S. Huang, E. A. Armstrong, S. Benavente, P. Chinnaiyan, P. M. Harari, Dual-agent molecular targeting of the epidermal growth factor receptor (EGFR): combining anti-EGFR antibody with tyrosine kinase inhibitor, Cancer Res. 64 (2004) 5355-5362.
[17] J. Graham, M. Muhsin, P. Kirkpatrick, Cetuximab, Nat. Rev. Drug Discov. 3 (2004) 549-550.
[18] N. I. Goldstein, M. Prewett, K. Zuklys, P. Rockwell, J. Mendelsohn, Biological efficacy of a chimeric antibody to the epidermal growth factor receptor in a human tumor xenograft model, Clin. Cancer Res. 1 (1995) 1311-1318.
[19] J. R. Bischoff, D. H. Kim, A. Williams, C. Heise, S. Horn, M. Muna, L. Ng, J. A. Nye, A. Sampson-Johannes, A. Fattaey, F. McCormick, An adenovirus mutant that replicates selectively in p53-deficient human tumor cells, Science 274 (1996) 373-376.
[20] D. Kim, Replication-selective oncolytic adenoviruses: virotherapy aimed at genetic targets in cancer, Oncogene 19 (2000) 6660-6669.
[21] R. Vile, Cancer gene therapy—new approaches to tumour cell killing, J. Gene Med. 2 (2000) 141-143.
[22] J. S. Lee, E. Oh, J. Y. Yoo, K. S. Choi, M. J. Yoon, C. O. Yun, Adenovirus expressing dual c-Met-specific shRNA exhibits potent antitumor effect through autophagic cell death accompanied by senescence-like phenotypes in glioblastoma cells, Oncotarget 6 (2015) 4051-4065.
[23] A. S. Nigatu, S. Vupputuri, N. Flynn, B. J. Neely, J. D. Ramsey, Evaluation of cellpenetrating peptide/adenovirus particles for transduction of CAR-negative cells, J. Pharm. Sci. 102 (2013) 1981-1993.
[24] A. Kanerva, A. Hemminki, Modified adenoviruses for cancer gene therapy, Int. J. Cancer 110 (2004) 475-480.
[25] O. J. Kwon, E. Kang, J. W. Choi, S. W. Kim, C. O. Yun, Therapeutic targeting of chitosan-PEG-folate-complexed oncolytic adenovirus for active and systemic cancer gene therapy, J. Control. Release 169 (2013) 257-265.
[26] A. H. Baker, S. A. Nicklin, D. M. Shayakhmetov, FX and host defense evasion tactics by adenovirus, Mol. Ther. 21 (2013) 1109-1111.
[27] M. D. Wheeler, S. Yamashina, M. Froh, I. Rusyn, R. G. Thurman, Adenoviral gene delivery can inactivate Kupffer cells: role of oxidants in NF-kappaB activation and cytokine production, J. Leukoc. Biol. 69 (2001) 622-630.

[28] E. Kang, C. O. Yun, Current advances in adenovirus nanocomplexes: more specificity and less immunogenicity, BMB Rep. 43 (2010) 781-788.

[29] P. H. Kim, J. H. Sohn, J. W. Choi, Y. Jung, S. W. Kim, S Haam, C. O. Yun, Active targeting and safety profile of PEG-modified adenovirus conjugated with herceptin, Biomaterials 32 (2011) 2314-2326.

[30] D. H. Thompson, Adenovirus in a synthetic membrane wrapper: an example of hybrid vigor? ACS Nano 2 (2008) 821-826.

[31] R. Singh, K. Kostarelos, Designer adenoviruses for nanomedicine and nanodiagnostics, Trends Biotechnol. 27 (2009) 220-229.

[32] K. D. Fisher, L. W. Seymour, HPMA copolymers for masking and retargeting of therapeutic viruses, Adv. Drug Deliv. Rev. 62 (2010) 240-245.

[33] A. Vetter, K. S. Virdi, S. Espenlaub, W. Rodl, E. Wagner, P. S. Holm, C. Scheu, F. Kreppel, C. Spitzweg, M. Ogris, Adenoviral vectors coated with PAMAM dendrimer conjugates allow CAR independent virus uptake and targeting to the EGF receptor, Mol. Pharm. 10 (2013) 606-618.

[34] G. K. Grunwald, A. Vetter, K. Klutz, M. J. Willhauck, N. Schwenk, R. Senekowitsch-Schmidtke, M. Schwaiger, C. Zach, E. Wagner, B. Goke, P. S. Holm, M. Ogris, C. Spitzweg, Systemic image-guided liver cancer radiovirotherapy using dendrimercoated adenovirus encoding the sodium iodide symporter as theranostic gene, J. Nucl. Med. 54 (2013) 1450-1457.

[35] T. G. Park, J. H. Jeong, S. W. Kim, Current status of polymeric gene delivery systems, Adv. Drug Deliv. Rev. 58 (2006) 467-486.

[36] P. Chollet, M. C. Favrot, A. Hurbin, J. L. Coll, Side-effects of a systemic injection of linear polyethylenimine-DNA complexes, J. Gene Med. 4 (2002) 84-91.

[37] S. Goldoni, R. V. Iozzo, Tumor microenvironment: modulation by decorin and related molecules harboring leucine-rich tandem motifs, Int. J. Cancer 123 (2008) 2473-2479.

[38] Y. Hu, H. Sun, R. T. Owens, J. Wu, Y. Q. Chen, I. M. Berquin, D. Perry, J. T. O'Flaherty, I. J. Edwards, Decorin suppresses prostate tumor growth through inhibition of epidermal growth factor and androgen receptor pathways, Neoplasia 11 (2009) 1042-1053.

[39] P. C. Ma, M. S. Tretiakova, V. Nallasura, R. Jagadeeswaran, A. N. Husain, R. Salgia, Downstream signalling and specific inhibition of c-MET/HGF pathway in small cell lung cancer: implications for tumour invasion, Br. J. Cancer 97 (2007) 368-377.

[40] J. Kim, J. H. Kim, K. J. Choi, P. H. Kim, C. O. Yun, E1A- and E1B-Double mutant replicating adenovirus elicits enhanced oncolytic and antitumor effects, Hum. Gene Ther. 18 (2007) 773-786.

[41] I. K. Choi, Y. S. Lee, J. Y. Yoo, A. R. Yoon, H. Kim, D. S. Kim, D. G. Seidler, J. H. Kim, C. O. Yun, Effect of decorin on overcoming the extracellular matrix barrier for oncolytic virotherapy, Gene Ther. 17 (2010) 190-201.

[42] J. S. Lee, M. W. Hur, S. K. Lee, W. I. Choi, Y. G. Kwon, C. O. Yun, A novel sLRP6E1E2 inhibits canonical Wnt signaling, epithelial-to-mesenchymal transition, and induces mitochondria-dependent apoptosis in lung cancer, PLoS One 7 (2012), e36520.

[43] M. Green, M. Pina, R. Kimes, P. C. Wensink, L. A. MacHattie, C. A. Thomas Jr., Adenovirus DNA. I. Molecular weight and conformation, Proc. Natl. Acad. Sci. U.S.A 57 (1967) 1302-1309.

[44] S. Zhu, M. Hong, G. Tang, L. Qian, J. Lin, Y. Jiang, Y. Pei, Partly PEGylated polyamidoamine dendrimer for tumor-selective targeting of doxorubicin: the effects of PEGylation degree and drug conjugation style, Biomaterials 31 (2010) 1360-1371.

[45] M. Wang, C. C. Mi, W. X. Wang, C. H. Liu, Y. F. Wu, Z. R. Xu, C. B. Mao, S. K. Xu, Immunolabeling and NIR-excited fluorescent imaging of HeLa cells by using NaYF(4):Yb,Er upconversion nanoparticles, ACS Nano 3 (2009) 1580-1586.

[46] J. Lee, K. S. Yun, C. S. Choi, S. H. Shin, H. S. Ban, T. Rhim, S K Lee, K. Y. Lee, T cell-specific siRNA delivery using antibody-conjugated chitosan nanoparticles, Bioconjug. Chem. 23 (2012) 1174-1180.

[47] Y. Na, J. W. Choi, D. Kasala, J. Hong, E. Oh, Y. Li, S. J. Jung, S. W. Kim, C. O. Yun, Potent antitumor effect of neurotensin receptor-targeted oncolytic adenovirus co-expressing decorin and Wnt antagonist in an orthotopic pancreatic tumor model, J. Control. Release: official journal of the Controlled Release Society (2015).

[48] J. Kim, P. H. Kim, H. Y. Nam, J. S. Lee, C. O. Yun, S. W. Kim, Linearized oncolytic adenoviral plasmid DNA delivered by bioreducible polymers, J. Control. Release 158 (2012) 451-460.

[49] S. Zhu, M. Hong, L. Zhang, G. Tang, Y. Jiang, Y. Pei, PEGylated PAMAM dendrimerdoxorubicin conjugates: in vitro evaluation and in vivo tumor accumulation, Pharm. Res. 27 (2010) 161-174.

[50] S. Karlin, V. Brendel, Charge configurations in viral proteins, Proc. Natl. Acad. Sci. U.S.A 85 (1988) 9396-9400.

[51] R. Bazak, M. Houri, S. E. Achy, W. Hussein, T. Refaat, Passive targeting of nanoparticles to cancer: a comprehensive review of the literature, Mol. Clin. Oncol. 2 (2014) 904-908.

[52] W. Jiang, B. Y. Kim, J. T. Rutka, W. C. Chan, Nanoparticle-mediated cellular response is size-dependent, Nat. Nanotechnol. 3 (2008) 145-150.

[53] J. W. Choi, S. J. Jung, D. Kasala, J. K. Hwang, J. Hu, Y. H. Bae, C. O. Yun, pH-sensitive oncolytic adenovirus hybrid targeting acidic tumor microenvironment and angiogenesis, J. Control. Release 205 (2015) 134-143.

[54] C. H. Lee, D. Kasala, Y. Na, M. S. Lee, S. W. Kim, J. H. Jeong, C. O. Yun, Enhanced therapeutic efficacy of an adenovirus-PEI-bile-acid complex in tumors with low Coxsackie and adenovirus receptor expression, Biomaterials 35 (2014) 5505-5516.

[55] M. Perez-Torres, M. Guix, A. Gonzalez, C. L. Arteaga, Epidermal growth factor receptor (EGFR) antibody down-regulates mutant receptors and inhibits tumors expressing EGFR mutations, J. Biol. Chem. 281 (2006) 40183-40192.

[56] E. Schonherr, C. Sunderkotter, R. V. Iozzo, L. Schaefer, Decorin, a novel player in the insulin-like growth factor system, J. Biol. Chem. 280 (2005) 15767-15772.

[57] S. Buraschi, N. Pal, N. Tyler-Rubinstein, R. T. Owens, T. Neill, R. V. Iozzo, Decorin antagonizes Met receptor activity and down-regulates beta-catenin and Myc levels, J. Biol. Chem. 285 (2010) 42075-42085.

[58] O. J. Kwon, P. H. Kim, S. Huyn, L. Wu, M. Kim, C. O. Yun, A hypoxia- and alpha-fetoprotein-dependent oncolytic adenovirus exhibits specific killing of hepatocellular carcinomas, Clin. Cancer Res. 16 (2010) 6071-6082.

[59] R. Alemany, D. T. Curiel, CAR-binding ablation does not change biodistribution and toxicity of adenoviral vectors, Gene Ther. 8 (2001) 1347-1353.

[60] C. R. O'Riordan, A. Lachapelle, C. Delgado, V. Parkes, S. C. Wadsworth, A. E. Smith, G. E. Francis, PEGylation of adenovirus with retention of infectivity and protection from neutralizing antibody in vitro and in vivo, Hum. Gene Ther. 10 (1999) 1349-1358.

[61] H. Mok, D. J. Palmer, P. Ng, M. A. Barry, Evaluation of polyethylene glycolmodification of first-generation and helper-dependent adenoviral vectors to reduce innate immune responses, Mol. Ther. 11 (2005) 66-79.

[62] S. Bramante, J. K. Kaufmann, V. Veckman, I. Liikanen, D. M. Nettelbeck, O. Hemminki, L. Vassilev, V. Cerullo, M. Oksanen, R. Heiskanen, T. Joensuu, A. Kanerva, S. Pesonen, S. Matikainen, M. Vaha-Koskela, A. Koski, A. Hemminki, Treatment of melanoma with a serotype 5/3 chimeric oncolytic adenovirus coding for GM-CSF: results in vitro, in rodents and in humans, Int. J. Cancer 137 (2015) 1775-1783.

[63] R. Carlisle, J. Choi, M. Bazan-Peregrino, R. Laga, V. Subr, L. Kostka, K. Ulbrich, C. C. Coussios, L. W. Seymour, Enhanced tumor uptake and penetration of virotherapy using polymer stealthing and focused ultrasound, J. Natl. Cancer Inst. 105 (2013) 1701-1710.

[64] X. F. Fei, Q. B. Zhang, J. Dong, Y. Diao, Z. M. Wang, R. J. Li, Z. C. Wu, A. D. Wang, Q. Lan, S. M. Zhang, Q. Huang, Development of clinically relevant orthotopic xenograft mouse model of metastatic lung cancer and glioblastoma through surgical tumor tissues injection with trocar, J. Exp. Clin. Cancer Res. 29 (2010) 84.

[65] A. Koski, M. Rajecki, K. Guse, A. Kanerva, A. Ristimaki, S. Pesonen, S. Escuteniare, A. Hemminki, Systemic adenoviral gene delivery to orthotopic murine breast tumors with ablation of coagulation factors, thrombocytes and Kupffer cells, J. Gene Med. 11 (2009) 966-977.

[66] J. M. Prill, S. Espenlaub, U. Samen, T. Engler, E. Schmidt, F. Vetrini, A. Rosewell, N. Grove, D. Palmer, P. Ng, S. Kochanek, F. Kreppel, Modifications of adenovirus hexon allow for either hepatocyte detargeting or targeting with potential evasion from Kupffer cells, Mol Ther. 19 (2011) 83-92.

[67] F. M. Klion, F. Schaffner, The ultrastructure of acidophilic "Councilman-like" bodies in the liver, Am. J. Pathol. 48 (1966) 755-767.

What is claimed is:

1. A virus-polymer complex in which a polymer binds to a surface of a virus, wherein the polymer is poly(amidoamine) (PAMAM) to which PEG and Cetuximab are conjugated.

2. The polymer-virus complex of claim 1, wherein the virus is any one selected from a group consisting of adeno-associated virus (AAV), a retrovirus, a lentivirus, herpes simplex virus, vaccinia virus, a reovirus, a poxvirus, and the Semliki forest virus.

3. The polymer-virus complex of claim 2, wherein the virus is an adenovirus.

4. The polymer-virus complex of claim 1, wherein the virus-polymer complex has a virus:polymer molar ratio of 1: more than $1\times10^4$ to less than $1\times10^6$.

5. A pharmaceutical composition comprising: a therapeutically effective amount of the polymer-virus complex of claim 1; a therapeutic gene; and a pharmaceutically acceptable carrier.

6. The pharmaceutical composition of claim 5, wherein the virus is any one selected from a group consisting of adeno-associated virus, a retrovirus, a lentivirus, herpes simplex virus, vaccinia virus, a reovirus, a poxvirus, and the Semliki forest virus.

7. The pharmaceutical composition of claim 5, wherein the virus is an adenovirus.

8. The pharmaceutical composition of claim 5, wherein the virus-polymer complex has a virus:polymer molar ratio of 1: more than $1\times10^4$ to less than $1\times10^6$.

9. The pharmaceutical composition of claim 5, wherein the composition is an anticancer composition.

10. The pharmaceutical composition of claim 9, wherein the cancer is laryngeal cancer, lung cancer, non-small cell lung cancer, colon cancer, bone cancer, pancreatic cancer, skin cancer, head or neck cancer, ovarian cancer, uterine cancer, rectal cancer, gastric cancer, anal cancer, breast cancer, fallopian tube cancer, endometrial cancer, cervical cancer, vaginal cancer, vulva cancer, Hodgkin's disease, esophageal cancer, small intestine cancer, endocrine cancer, thyroid cancer, parathyroid cancer, adrenal gland cancer, soft tissue sarcoma, urethral cancer, penile cancer, prostate cancer, chronic or acute leukemia, lymphocytic lymphoma, bladder cancer, renal or hydroureter cancer, renal cell carcinoma, renal pelvic carcinoma, a central nervous system (CNS) tumor, primary central nervous system lymphoma, a spinal cord tumor, liver cancer, bronchial cancer, nasopharyngeal cancer, brain stem glioma, or pseudomyxoma, Hepatoblastoma, Testicular cancer, Glioblastoma, lip cancer, Ovarian germ cell tumor, Basal cell carcinoma, Multiple myeloma, Gallbladder cancer, Choroidal melanoma, carcinoma of the ampulla of Vater, Peritoneal cancer, tongue cancer, Small cell carcinoma, pediatric lymphoma, neuroblastoma, duodenal cancer, ureteral cancer, astrocytoma, meningioma, renal pelvic cancer, pudendum cancer, thymus cancer, pituitary adenoma, or the like, but is not limited thereto.

11. A composition for gene delivery, comprising the polymer-virus complex of claim 1.

12. The composition of claim 11, wherein the virus-polymer complex has a virus:polymer molar ratio of 1: more than $1\times10^4$ to less than $1\times10^6$.

13. A method for treating cancer comprising administrating a therapeutically effective amount of the polymer-virus complex of claim 1; a therapeutic gene; and a pharmaceutically acceptable carrier to a subject.

14. A method for delivering genes comprising administrating a therapeutically effective amount of the polymer-virus complex of claim 1; and a therapeutic gene to a subject.

* * * * *